US012544055B2

(12) United States Patent
Swift et al.

(10) Patent No.: US 12,544,055 B2
(45) Date of Patent: *Feb. 10, 2026

(54) ILLUMINATED DUAL-BLADE RETRACTOR

(71) Applicant: CooperSurgical, Inc., Trumbull, CT (US)

(72) Inventors: Jason Swift, Newburyport, MA (US); Demetrio D. Anaya, Somerville, MA (US); Jeffrey Ralph Swift, Boca Grande, FL (US); Nicholas Lauder, Medford, MA (US)

(73) Assignee: CooperSurgical, Inc., Trumbull, CT (US)

( * ) Notice: Subject to any disclaimer, the term of this patent is extended or adjusted under 35 U.S.C. 154(b) by 87 days.

This patent is subject to a terminal disclaimer.

(21) Appl. No.: 18/180,937

(22) Filed: Mar. 9, 2023

(65) Prior Publication Data

US 2023/0218285 A1 Jul. 13, 2023

Related U.S. Application Data

(63) Continuation of application No. 17/192,935, filed on Mar. 5, 2021, now Pat. No. 11,622,758, which is a (Continued)

(51) Int. Cl.

| | |
|---|---|
| ***A61B 17/02*** | (2006.01) |
| ***A61B 90/30*** | (2016.01) |
| *A61B 17/00* | (2006.01) |

(52) U.S. Cl.

CPC .......... *A61B 17/0218* (2013.01); *A61B 90/30* (2016.02); *A61B 2017/00734* (2013.01); *A61B 2218/008* (2013.01); *A61B 2560/0214* (2013.01)

(58) Field of Classification Search

CPC .......... A61B 90/30; A61B 2017/00734; A61B 2218/008; A61B 2560/0214; (Continued)

(56) References Cited

U.S. PATENT DOCUMENTS

| | | | |
|---|---|---|---|
| 559,122 | A | 4/1896 | Daily |
| 659,182 | A | 10/1900 | Pilling |

(Continued)

FOREIGN PATENT DOCUMENTS

| | | | |
|---|---|---|---|
| CN | 2239235 | Y | 11/1996 |
| CN | 2265156 | Y | 10/1997 |

(Continued)

OTHER PUBLICATIONS

International Search Report for International application No. PCT/US2021/017768 issued May 27, 2021.

(Continued)

*Primary Examiner* — Tessa M Matthews
(74) *Attorney, Agent, or Firm* — Fish & Richardson P.C.

(57) ABSTRACT

A portable dual-blade retractor comprising a handle having a first end and a second end, a first blade extending from the first end of the handle, a second blade extending from the second end of the handle, and an illumination assembly including (a) one or more first direct light sources provided on the first blade and (b) one or more second direct light sources provided on the second blade, wherein the first and second direct light sources are individually controlled.

25 Claims, 12 Drawing Sheets

Related U.S. Application Data continuation of application No. 16/800,227, filed on Feb. 25, 2020, now Pat. No. 10,966,702.

(58) Field of Classification Search
CPC ............ A61B 17/7043; A61B 17/7049; A61B 17/705; A61B 17/7052; A61B 17/0218
See application file for complete search history.

(56) References Cited

U.S. PATENT DOCUMENTS 2,235,979 A 3/1941 Brown
2,247,458 A 7/1941 Wintemberg
2,482,971 A 9/1949 Golson
2,592,190 A 4/1952 Rubens et al.
3,324,850 A 6/1967 Gunning et al.
3,332,414 A 7/1967 Gasper
3,532,088 A 10/1970 Fiore
3,592,199 A 7/1971 Ostensen
3,595,222 A 7/1971 Vellacott
3,638,644 A 2/1972 Reick
3,650,266 A 3/1972 Pestka et al.
3,675,641 A 7/1972 Fiore
3,716,047 A 2/1973 Moore et al.
3,729,006 A 4/1973 Wilder et al.
3,762,400 A 10/1973 McDonald
3,769,968 A 11/1973 Blount et al.
3,789,835 A 2/1974 Whitman
3,815,585 A 6/1974 Fiore
3,826,248 A 7/1974 Gobels
3,851,642 A 12/1974 McDonald
3,934,578 A 1/1976 Heine
3,945,371 A 3/1976 Adelman
3,978,850 A 9/1976 Moore et al.
4,067,323 A 1/1978 Troutner
4,156,424 A 5/1979 Burgin
4,210,133 A 7/1980 Castaneda
4,226,228 A 10/1980 Shin et al.
4,263,899 A 4/1981 Burgin
4,300,541 A 11/1981 Burgin
4,337,763 A 7/1982 Petrassevich
4,432,351 A 2/1984 Hoary
4,492,220 A 1/1985 Hayes
4,502,468 A 3/1985 Burgin
4,527,553 A 7/1985 Upsher
4,546,761 A 10/1985 McCullough
4,551,129 A 11/1985 Coleman et al.
4,562,832 A 1/1986 Wilder
4,566,439 A 1/1986 Burgin
4,574,784 A 3/1986 Soloway
4,597,383 A 7/1986 Van Der Bel
4,607,623 A 8/1986 Bauman
4,619,248 A 10/1986 Walsh
4,638,792 A 1/1987 Burgin
4,759,349 A 7/1988 Betz et al.
4,766,887 A 8/1988 Cecil, Jr. et al.
4,807,600 A 2/1989 Hayes
4,884,559 A 12/1989 Collins
4,905,670 A 3/1990 Adair
4,934,352 A 6/1990 Sullivan, Jr.
4,971,036 A 11/1990 Collins
5,018,507 A 5/1991 Montaldi
5,026,368 A 6/1991 Adair
5,054,906 A 10/1991 Lyons, Jr.
5,063,908 A * 11/1991 Collins .................... A61B 1/32
600/187
5,143,054 A 9/1992 Adair
5,165,387 A 11/1992 Woodson
5,174,278 A 12/1992 Babkow
5,179,937 A 1/1993 Lee
5,179,938 A 1/1993 Lonky
5,222,271 A 6/1993 Eganhouse
D337,384 S 7/1993 Schucman
5,231,973 A 8/1993 Dickie
5,318,009 A 6/1994 Robinson
5,329,938 A 7/1994 Lonky
5,427,152 A 6/1995 Weber
5,438,976 A 8/1995 Nash
5,465,709 A 11/1995 Dickie et al.
5,499,964 A 3/1996 Beck et al.
5,512,038 A 4/1996 O'Neal et al.
5,553,627 A 9/1996 Newkirk
5,695,492 A 12/1997 Brown
5,716,329 A 2/1998 Dieter
5,785,648 A 7/1998 Min
5,840,013 A 11/1998 Lee et al.
5,846,249 A 12/1998 Thompson
5,865,729 A 2/1999 Meehan
5,873,820 A 2/1999 Norell
5,879,304 A 3/1999 Schuchman et al.
5,888,195 A 3/1999 Schneider
5,899,854 A 5/1999 Slishman
5,902,315 A 5/1999 Dubois
5,916,150 A 6/1999 Sillman
5,967,971 A 10/1999 Bolser
6,001,077 A 12/1999 Ellman et al.
6,004,265 A 12/1999 Hsu et al.
6,036,638 A 3/2000 Nwawka
6,036,713 A 3/2000 Kieturakis
6,048,308 A 4/2000 Strong
6,080,105 A 6/2000 Spears
6,130,520 A 10/2000 Wawro et al.
6,176,824 B1 1/2001 Davis
6,186,944 B1 2/2001 Tsai
6,193,653 B1 2/2001 Evans et al.
6,217,512 B1 4/2001 Salo et al.
6,231,505 B1 5/2001 Martin
6,231,506 B1 5/2001 Hu et al.
6,254,247 B1 7/2001 Carson
6,277,067 B1 8/2001 Blair
6,319,199 B1 11/2001 Sheehan et al.
6,346,085 B1 2/2002 Schiffman
6,359,644 B1 3/2002 Salvati
6,361,489 B1 3/2002 Tsai
6,363,763 B1 4/2002 Geringer et al.
6,379,296 B1 4/2002 Baggett
6,379,299 B1 4/2002 Borodulin et al.
6,394,111 B1 5/2002 Jacobs et al.
6,394,950 B1 5/2002 Weiss
6,413,208 B1 7/2002 Schöllhorn et al.
6,416,465 B2 7/2002 Brau
6,428,180 B1 8/2002 Karram et al.
6,432,045 B2 8/2002 Lemperle et al.
6,432,049 B1 8/2002 Banta
6,436,033 B2 8/2002 Tan
6,450,952 B1 9/2002 Rioux
6,468,206 B1 10/2002 Hipps et al.
6,468,232 B1 10/2002 Ashton-Miller et al.
6,487,440 B2 11/2002 Deckert et al.
6,504,985 B2 1/2003 Parker et al.
6,523,973 B2 2/2003 Galli
6,524,259 B2 2/2003 Baxter-Jones et al.
6,569,089 B1 5/2003 Covington et al.
6,569,091 B2 5/2003 Diokno et al.
6,589,168 B2 7/2003 Thompson
6,595,917 B2 7/2003 Nieto
6,616,603 B1 9/2003 Fontana
6,626,825 B2 9/2003 Tsai
6,663,576 B2 12/2003 Gombrich et al.
6,676,598 B2 1/2004 Rudischhauser et al.
6,719,688 B2 4/2004 Pecherer et al.
6,761,687 B1 7/2004 Doshi
6,830,547 B2 12/2004 Weiss
6,896,653 B1 5/2005 Vail, III et al.
7,014,340 B2 3/2006 Betis
7,029,439 B2 4/2006 Roberts et al.
D520,464 S 5/2006 Strong
7,223,223 B2 5/2007 Lindsay
7,276,025 B2 10/2007 Roberts et al.
7,306,559 B2 12/2007 Williams
7,474,820 B2 1/2009 Vayser et al.
7,492,116 B2 2/2009 Oleynikov et al.
7,510,524 B2 3/2009 Vayser et al.
7,631,981 B2 12/2009 Miller et al.
7,736,304 B2 6/2010 Pecherer

(56) References Cited

U.S. PATENT DOCUMENTS 7,758,203 B2 7/2010 McMahon et al.
7,845,824 B2 12/2010 Robotham
7,878,973 B2 2/2011 Yee et al.
7,901,353 B2 3/2011 Vayser et al.
7,909,759 B2 3/2011 Pecherer
7,967,809 B2 6/2011 Jay-Robinson
8,012,089 B2 9/2011 Bayat
8,047,987 B2 11/2011 Grey et al.
8,052,702 B2 11/2011 Hess et al.
8,088,066 B2 1/2012 Grey et al.
8,096,945 B2 1/2012 Buchok et al.
8,142,352 B2 3/2012 Vivenzio et al.
8,142,353 B2 3/2012 Pecherer et al.
8,157,728 B2 4/2012 Danna et al.
8,162,824 B2 4/2012 Vayser et al.
8,162,826 B2 4/2012 Pecherer et al.
8,251,898 B2 8/2012 Pecherer
8,285,093 B2 10/2012 Vayser et al.
8,292,805 B2 10/2012 Vayser et al.
8,317,693 B2 11/2012 Grey et al.
8,388,523 B2 3/2013 Vivenzio et al.
8,394,017 B2 3/2013 Kieffer
8,435,175 B2 5/2013 McMahon et al.
8,459,844 B2 6/2013 Lia et al.
8,512,234 B2 8/2013 Grey et al.
8,512,237 B2 8/2013 Bastia
8,555,892 B2 10/2013 Traub
8,594,472 B2 11/2013 Vayser et al.
8,596,847 B2 12/2013 Vayser et al.
8,628,879 B2 1/2014 Pecherer et al.
8,651,704 B1 2/2014 Gordin et al.
8,708,896 B2 4/2014 Vayser et al.
8,786,210 B2 7/2014 Delucia
8,795,162 B2 8/2014 Vayser et al.
8,821,385 B2 9/2014 Naito
8,870,761 B2 10/2014 Vayser et al.
8,890,489 B2 11/2014 Wood
D719,652 S 12/2014 Swift
8,899,809 B2 12/2014 Vayser et al.
8,979,745 B2 3/2015 Swift
9,002,159 B2 4/2015 Sutherland et al.
9,005,115 B2 4/2015 Vayser
9,044,161 B2 6/2015 Vayser et al.
9,050,048 B2 6/2015 Nadershahi
9,072,452 B2 7/2015 Vayser et al.
9,072,455 B2 7/2015 Vayser et al.
D745,669 S 12/2015 Swift
9,198,566 B2 12/2015 Lia et al.
9,229,165 B2 1/2016 Vayser et al.
9,241,617 B2 1/2016 Grey et al.
D752,217 S 3/2016 Swift
9,271,709 B2 3/2016 Grey et al.
9,271,710 B2 3/2016 Grey et al.
9,282,878 B2 * 3/2016 Grey .................. A61B 1/00105
D753,295 S 4/2016 Vivenzio et al.
9,307,897 B2 4/2016 Swift
9,308,054 B2 4/2016 Vayser et al.
9,332,898 B2 5/2016 McMahon et al.
9,429,746 B2 8/2016 Vayser et al.
9,468,366 B2 10/2016 Grey et al.
9,504,373 B2 11/2016 Vayser et al.
9,510,737 B2 12/2016 Vayser et al.
9,532,706 B2 1/2017 McMahon et al.
9,574,742 B2 2/2017 Vayser et al.
9,629,529 B1 4/2017 Indovina et al.
9,636,004 B2 5/2017 Lia et al.
9,636,182 B2 5/2017 Vayser et al.
9,718,130 B1 8/2017 Vayser et al.
9,763,743 B2 9/2017 Lin et al.
9,808,231 B2 11/2017 Miraki et al.
9,814,377 B2 11/2017 Lia et al.
9,820,638 B2 11/2017 Cheng
9,820,729 B2 11/2017 Miles et al.
9,826,892 B2 11/2017 Dresher et al.
9,833,295 B2 12/2017 Vayser et al.
9,833,308 B2 12/2017 Dye
9,844,364 B2 12/2017 Grey et al.
9,861,349 B2 1/2018 Nadershahi et al.
9,867,531 B2 1/2018 Pacey et al.
9,867,602 B2 1/2018 Swift
9,877,639 B2 1/2018 Grey et al.
9,877,644 B2 1/2018 Greenstein et al.
D809,660 S 2/2018 Nguyen et al.
9,883,792 B2 2/2018 McMahon et al.
9,888,957 B2 2/2018 Wolf et al.
9,907,544 B2 3/2018 Nadershahi et al.
9,913,682 B2 3/2018 Wolf et al.
9,918,618 B2 3/2018 Molnar
9,918,802 B2 3/2018 Coppersmith et al.
9,931,028 B2 4/2018 Lia et al.
9,943,295 B2 4/2018 King
9,949,814 B2 4/2018 Alexander et al.
9,955,858 B2 5/2018 Pamnani et al.
9,968,262 B2 5/2018 Greenstein et al.
9,968,346 B2 5/2018 Alexander et al.
9,980,710 B2 5/2018 Seifert et al.
9,986,901 B2 6/2018 Grey et al.
9,986,903 B2 6/2018 Nadershahi et al.
9,986,988 B2 6/2018 Ferro et al.
9,999,345 B2 6/2018 Vayser et al.
10,004,392 B2 6/2018 Millard et al.
10,004,393 B2 6/2018 Kucklick
10,028,648 B2 7/2018 Goldfain et al.
10,028,649 B2 7/2018 Salvati et al.
10,028,780 B2 7/2018 Wolf et al.
10,045,686 B2 8/2018 Ou Yang et al.
10,045,731 B2 8/2018 Prasad et al.
10,052,432 B2 8/2018 Dexter et al.
10,064,611 B2 9/2018 Ross et al.
10,064,613 B2 9/2018 Davis et al.
10,068,173 B2 9/2018 Vayser et al.
10,092,176 B2 10/2018 Kienzle et al.
10,092,281 B2 10/2018 Perler et al.
10,098,530 B2 10/2018 McMahon et al.
10,105,043 B2 10/2018 George
10,117,646 B2 11/2018 Friedrich et al.
10,130,441 B2 11/2018 Martinez
10,166,016 B2 1/2019 Shimizu et al.
10,172,601 B2 1/2019 Ahn
10,174,933 B2 1/2019 Phillips, Jr. et al.
10,188,298 B2 1/2019 Greenstein et al.
10,213,271 B2 2/2019 Duggal et al.
10,219,800 B2 3/2019 Tsubouchi
10,220,445 B2 3/2019 Vayser et al.
10,226,555 B2 3/2019 Vayser et al.
10,238,462 B2 3/2019 Wood et al.
D846,119 S 4/2019 Greeley et al.
10,278,571 B2 5/2019 Poormand
10,292,782 B2 5/2019 Haverich et al.
10,292,784 B2 5/2019 Duggal et al.
10,321,969 B2 6/2019 Wayne et al.
10,342,525 B2 7/2019 Wilson
10,456,190 B2 10/2019 Vayser et al.
10,499,974 B2 12/2019 Heim et al.
10,500,010 B2 12/2019 Vayser et al.
10,512,518 B2 12/2019 Vayser et al.
10,512,520 B2 12/2019 Wayne et al.
10,531,933 B2 1/2020 Vayser et al.
10,548,682 B2 2/2020 Vayser et al.
10,568,712 B2 2/2020 Vayser et al.
10,675,115 B2 6/2020 Vayser et al.
10,729,511 B2 8/2020 Vayser et al.
10,729,512 B2 8/2020 Wayne et al.
11,540,817 B2 1/2023 Gallagher et al.
11,622,758 B2 4/2023 Swift et al.
11,744,568 B2 9/2023 Swift et al.
2001/0029044 A1 10/2001 Gombrich et al.
2002/0009275 A1 1/2002 Williams et al.
2002/0022769 A1 2/2002 Smith et al.
2002/0038075 A1 3/2002 Tsai
2002/0038076 A1 3/2002 Sheehan et al.
2002/0055670 A1 5/2002 Weiss
2002/0115909 A1 8/2002 Bolser
2002/0156350 A1 10/2002 Nieto

(56) References Cited

U.S. PATENT DOCUMENTS

2002/0165435 A1 11/2002 Weiss
2002/0198471 A1 12/2002 Baxter-Jones et al.
2003/0095781 A1* 5/2003 Williams ........... A61B 17/2812 385/901
2003/0105387 A1 6/2003 Frumovitz et al.
2003/0139673 A1 7/2003 Vivenzio et al.
2003/0158502 A1 8/2003 Baxter-Jones et al.
2003/0176772 A1 9/2003 Yang
2003/0187331 A1 10/2003 Faludi et al.
2004/0026829 A1 2/2004 Van Der Weegen
2004/0054260 A1 3/2004 Klaassen et al.
2004/0141175 A1 7/2004 Baldwin et al.
2004/0183482 A1 9/2004 Roberts et al.
2004/0184288 A1 9/2004 Bettis
2004/0186355 A1 9/2004 Strong
2004/0254428 A1 12/2004 Ritland
2005/0065496 A1 3/2005 Simon et al.
2005/0085699 A1 4/2005 Weiss
2005/0085723 A1 4/2005 Huebner
2005/0093718 A1 5/2005 Martin
2005/0125015 A1 6/2005 McNally-Heintzelman et al.
2005/0159649 A1 7/2005 Patel
2005/0182301 A1 8/2005 Acker et al.
2005/0192482 A1 9/2005 Carpenter
2005/0215858 A1 9/2005 Vail, III
2005/0240081 A1 10/2005 Eliachar
2005/0277811 A1 12/2005 Richards et al.
2006/0084843 A1 4/2006 Sommerich et al.
2006/0122463 A1 6/2006 Klaassen
2006/0155276 A1 7/2006 Walulik et al.
2006/0189847 A1 8/2006 Yee et al.
2006/0200186 A1 9/2006 Marchek et al.
2007/0043264 A1 2/2007 Gillis et al.
2007/0060795 A1 3/2007 Vayser et al.
2007/0060938 A1 3/2007 Dziadik et al.
2007/0066872 A1 3/2007 Morrison et al.
2007/0100212 A1 5/2007 Pimenta et al.
2007/0208226 A1 9/2007 Grey et al.
2007/0230164 A1 10/2007 Vivenzio et al.
2007/0230167 A1 10/2007 McMahon et al.
2007/0255110 A1 11/2007 Wax et al.
2007/0270866 A1 11/2007 Von Jako
2007/0287888 A1 12/2007 Lovell et al.
2008/0002426 A1 1/2008 Vayser et al.
2008/0027461 A1 1/2008 Vaquero et al.
2008/0108877 A1 5/2008 Bayat
2008/0113312 A1 5/2008 Ortega
2008/0221569 A1 9/2008 Moore et al.
2008/0228038 A1 9/2008 McMahon et al.
2008/0269564 A1 10/2008 Gelnett
2008/0269565 A1 10/2008 McMahon et al.
2008/0278936 A1 11/2008 Kurth et al.
2009/0018400 A1 1/2009 Raymond et al.
2009/0069634 A1 3/2009 Larkin
2009/0097236 A1 4/2009 Miller et al.
2009/0112068 A1 4/2009 Grey et al.
2009/0275803 A1 11/2009 Krauter et al.
2009/0287192 A1 11/2009 Vivenzio et al.
2009/0312610 A1 12/2009 Buchok et al.
2010/0036382 A1 2/2010 Bonnadier
2010/0041955 A1 2/2010 Grey et al.
2010/0097794 A1 4/2010 Teng et al.
2010/0190129 A1 7/2010 Paz
2010/0191062 A1 7/2010 Kieffer
2010/0292533 A1 11/2010 Kasahara et al.
2011/0275894 A1 11/2011 Mackin
2012/0055470 A1 3/2012 Pecherer et al.
2012/0059226 A1 3/2012 Funt
2012/0078060 A1 3/2012 Swift
2012/0116170 A1 5/2012 Vayser et al.
2012/0232352 A1 9/2012 Lin et al.
2012/0243212 A1 9/2012 Smith et al.
2013/0018230 A1 1/2013 Su et al.
2013/0021798 A1 1/2013 Chen et al.
2013/0041229 A2 2/2013 Hahn et al.
2013/0092421 A1* 4/2013 Kajiya ................. H05K 1/0206 174/252
2013/0102850 A1 4/2013 Fiorella
2013/0102887 A1 4/2013 Thompson et al.
2013/0109910 A1 5/2013 Alexander et al.
2013/0158345 A1 6/2013 Majlessi
2013/0197313 A1 8/2013 Wan
2013/0245381 A1 9/2013 Dang et al.
2013/0245657 A1 9/2013 Deville et al.
2013/0267786 A1 10/2013 Vayser et al.
2013/0281784 A1 10/2013 Ray
2013/0324801 A1 12/2013 Grey et al.
2014/0088371 A1 3/2014 Vayser et al.
2014/0179998 A1 6/2014 Pacey
2014/0202459 A1 7/2014 Iqbal
2014/0228875 A1 8/2014 Saadat
2014/0257039 A1 9/2014 Feldman
2014/0275790 A1 9/2014 Vivenzio et al.
2014/0309499 A1 10/2014 Swift
2014/0316211 A1 10/2014 Hermle
2014/0323800 A1 10/2014 Dye
2014/0323811 A1 10/2014 Desantis et al.
2014/0364695 A1 12/2014 Nadershahi et al.
2014/0371536 A1 12/2014 Miller et al.
2015/0018625 A1 1/2015 Miraki et al.
2015/0018627 A1 1/2015 Vayser et al.
2015/0157469 A1 6/2015 Prado et al.
2015/0238070 A1 8/2015 Lia et al.
2015/0285382 A1 10/2015 Kienreich et al.
2015/0297217 A1 10/2015 Huitema et al.
2016/0000305 A1 1/2016 Elbaz et al.
2016/0030128 A1 2/2016 Duggal et al.
2016/0038032 A1 2/2016 Dan
2016/0066915 A1 3/2016 Baber et al.
2016/0081833 A1 3/2016 Leblanc et al.
2016/0095506 A1 4/2016 Dan et al.
2016/0100751 A1 4/2016 Davis et al.
2016/0151058 A1 6/2016 Ferro et al.
2016/0302657 A1 10/2016 Hussey et al.
2016/0379504 A1* 12/2016 Bailey .................... G16H 40/63
2017/0007228 A1 1/2017 Costabile
2017/0020621 A1 1/2017 Huldin et al.
2017/0059400 A1 3/2017 Murphy et al.
2017/0065282 A1 3/2017 Mathis et al.
2017/0079518 A1 3/2017 Elbaz et al.
2017/0172404 A1 6/2017 McMahon et al.
2017/0172555 A1 6/2017 Shimizu et al.
2017/0181605 A1 6/2017 Lalli et al.
2017/0181607 A1 6/2017 Lalli et al.
2017/0181615 A1 6/2017 Vella et al.
2017/0181616 A1 6/2017 Vella et al.
2017/0224206 A1 8/2017 Vayser
2017/0231712 A1 8/2017 Vayser
2017/0296162 A1 10/2017 Wan
2017/0300623 A1 10/2017 Rosenblatt et al.
2017/0303903 A1 10/2017 De Koning et al.
2017/0347871 A1 12/2017 Wallace et al.
2017/0360423 A1 12/2017 Stevenson et al.
2018/0000469 A1 1/2018 Wood et al.
2018/0008137 A1 1/2018 Poormand
2018/0008138 A1 1/2018 Thommen et al.
2018/0008368 A1 1/2018 Duggal et al.
2018/0014721 A1 1/2018 Rullo et al.
2018/0014842 A1 1/2018 Shener-Irmakoglu
2018/0014900 A1 1/2018 Vayser et al.
2018/0036095 A1 2/2018 Vayser et al.
2018/0042596 A1 2/2018 Tsubouchi
2018/0064316 A1 3/2018 Charles et al.
2018/0064317 A1 3/2018 Tesar
2018/0078301 A1 3/2018 Vayser
2018/0116581 A1 5/2018 Prasad et al.
2018/0125336 A1 5/2018 Goldfarb et al.
2018/0125347 A1 5/2018 Czyzewski et al.
2018/0132710 A1 5/2018 Pacey et al.
2018/0132970 A1 5/2018 Ritter
2018/0153391 A1 6/2018 Mcmahon et al.
2018/0156448 A1 6/2018 Phillips, Jr. et al.
2018/0206832 A1 7/2018 Greeley et al.
2018/0228376 A1 8/2018 Greenstein et al.

(56) References Cited

U.S. PATENT DOCUMENTS

| | | | | |
|---|---|---|---|---|
| 2018/0228483 | A1 | 8/2018 | Duggal et al. | |
| 2018/0235444 | A1 | 8/2018 | Tsai | |
| 2018/0235592 | A1 | 8/2018 | Kass et al. | |
| 2018/0249902 | A1 | 9/2018 | Grey et al. | |
| 2018/0263480 | A1 | 9/2018 | Lalli et al. | |
| 2018/0271581 | A1 | 9/2018 | Ou Yang et al. | |
| 2018/0280011 | A1 | 10/2018 | Ferro et al. | |
| 2018/0296082 | A1 | 10/2018 | Salvati et al. | |
| 2018/0296204 | A1 | 10/2018 | Davis | |
| 2018/0317746 | A1 | 11/2018 | Lalli et al. | |
| 2018/0317752 | A1 | 11/2018 | Cybulski et al. | |
| 2018/0317902 | A1 | 11/2018 | Green et al. | |
| 2018/0328572 | A1 | 11/2018 | Kennedy et al. | |
| 2019/0038273 | A1 | 2/2019 | Perler et al. | |
| 2019/0049655 | A1 | 2/2019 | Zagatsky et al. | |
| 2019/0076138 | A1 | 3/2019 | Opperman | |
| 2019/0083079 | A1 | 3/2019 | Shimizu et al. | |
| 2019/0133432 | A1 | 5/2019 | Tsai | |
| 2019/0143006 | A1 | 5/2019 | Vayser et al. | |
| 2019/0143414 | A1 | 5/2019 | Vayser et al. | |
| 2019/0150422 | A1 | 5/2019 | Welch | |
| 2019/0150725 | A1 | 5/2019 | Ramanujam et al. | |
| 2019/0150739 | A1 | 5/2019 | Wawro et al. | |
| 2019/0150786 | A1 | 5/2019 | Vassallo et al. | |
| 2019/0167111 | A1 | 6/2019 | Greenstein et al. | |
| 2019/0167378 | A1 | 6/2019 | Wood et al. | |
| 2019/0190293 | A1 | 6/2019 | Wawro et al. | |
| 2019/0223708 | A1 | 7/2019 | Recanati et al. | |
| 2019/0254512 | A1 | 8/2019 | Spiertz | |
| 2019/0254771 | A1 | 8/2019 | Swift et al. | |
| 2019/0335988 | A1 | 11/2019 | Lia et al. | |
| 2019/0343379 | A1 | 11/2019 | Altamura | |
| 2019/0365217 | A1 | 12/2019 | Hegenberger | |
| 2020/0008694 | A1 | 1/2020 | Karla et al. | |
| 2020/0046216 | A1 | 2/2020 | Moein | |
| 2020/0046336 | A1* | 2/2020 | Swift | A61B 17/02 |
| 2020/0069171 | A1 | 3/2020 | Miller et al. | |
| 2020/0107714 | A1 | 4/2020 | Bar-Or et al. | |
| 2020/0253467 | A1 | 8/2020 | Lees, Jr. et al. | |
| 2020/0275831 | A1* | 9/2020 | Levitin | A61B 1/32 |
| 2020/0337541 | A1 | 10/2020 | Vivenzio et al. | |
| 2020/0360023 | A1 | 11/2020 | Bagley et al. | |
| 2021/0145270 | A1 | 5/2021 | Altamura | |

FOREIGN PATENT DOCUMENTS

| | | | |
|---|---|---|---|
| CN | 2516109 | Y | 10/2002 |
| CN | 2629738 | Y | 8/2004 |
| CN | 1565664 | A | 1/2005 |
| CN | 2668152 | Y | 1/2005 |
| CN | 1717195 | A | 1/2006 |
| CN | 101179982 | A | 5/2008 |
| CN | 201055387 | Y | 5/2008 |
| CN | 203591245 | U | 5/2008 |
| CN | 201139589 | Y | 10/2008 |
| CN | 102415869 | A | 4/2012 |
| CN | 103154793 | A | 6/2013 |
| CN | 302536685 | S | 8/2013 |
| CN | 103925266 | A | 7/2014 |
| CN | 203898367 | U | 10/2014 |
| CN | 102573700 | B | 12/2014 |
| DE | 2128855 | A | 12/1972 |
| DE | 10216618 | A1 | 1/2003 |
| DE | 202004002963 | U1 | 5/2004 |
| DE | 102005002220 | A1 | 10/2005 |
| DE | 202005019780 | U1 | 5/2006 |
| DE | 600 33 612 | T2 | 12/2007 |
| DE | 202010017638 | U | 5/2012 |
| EP | 0190014 | A2 | 8/1986 |
| EP | 1074224 | A2 | 7/2001 |
| FR | 2490478 | A1 | 3/1982 |
| GB | 2505463 | A | 5/2014 |
| RU | 2187972 | C2 | 8/2002 |
| RU | 2308873 | C2 | 10/2007 |
| WO | 9825512 | A1 | 6/1998 |
| WO | 0137739 | A1 | 5/2001 |
| WO | 01/62137 | A2 | 8/2001 |
| WO | 03082123 | A2 | 10/2003 |
| WO | 2004064624 | A1 | 8/2004 |
| WO | 2006107877 | A2 | 10/2006 |
| WO | 2006107878 | A2 | 10/2006 |
| WO | 2007/084641 | A2 | 7/2007 |
| WO | 2009/090383 | A2 | 7/2009 |
| WO | 2009137017 | A2 | 11/2009 |
| WO | 2013-044151 | A1 | 3/2013 |
| WO | 2014-041172 | A1 | 3/2014 |
| WO | WO 2015/164881 | | 10/2015 |
| WO | 2006121530 | A2 | 11/2016 |
| WO | 2016196788 | A1 | 12/2016 |

OTHER PUBLICATIONS

International Search Report for International application No. PCT/US2021/014076 issued Apr. 15, 2021.

https://web.archive.org/web/20160618175418/http://bihlermed.com:80/scintillant/; Home—Scintillant® Surgical Light : Scintillant® Surgical Light; printed Oct. 19, 2022 (One Page).

International Search Report for International application No. PCT/US2016/016154 issued May 19, 2016 for corresponding U.S. Appl. No. 14/614,413.

International Search Report, for International application No. PCT/US2016/035508 issued Sep. 15, 2016 for corresponding U.S. Appl. No. 15/171,581.

International Search Report for International application No. PCT/US2016/036833 issued Jan. 19, 2017.

An Office Action issued in U.S. Appl. No. 15/171,581, a which is enclosed.

A PCT Search Report issued in PCT Application No. PCT/US2017/042617.

A Nov. 1, 2017 Chinese Office Action, without an English Translation, that issued in Chinese Patent Application No. 201510543086.7.

The Jul. 16, 2018 Chinese Office Action, without an English Translation, that issued in Chinese Patent Application No. 201510543086.7.

Solvey, Techinical Data Sheet, Ixef 1022 polyarylamide, Feb. 13, 2015, pp. 1-5.

http://www.makeitfrom.com/material-properties/Polyetheretheketone-PEEK, printed on Oct. 9, 2016, pp. 1-9.

The above documents were cited in a European Search Report issued on Nov. 23, 2018, that issued in the corresponding European Patent Application No. 16747107.7.

The above patent was cited in a Oct. 29, 2018 Chinese Office Action, without an English Translation, that issued in Chinese Patent Application No. 201711159829.6.

International Search Report of PCT/US2018/054925, Oct. 9, 2018.

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

A Supplementary European Search Report issued on Apr. 24, 2019, that issued in European Patent Application No. 16804432.9.

OBP Medical—OfficeSPEC, Premier Speculum for In-Office Procedures published Nov. 30, 2009 (1 page).

OBP Medical—ER-SPEC OBGYN Brochure published Nov. 19, 2014 (2 pages).

OBP Medical—ER-SPEC Brochure, Light Source Now 10X Brighter published Oct. 30, 2012 (1 page).

OBP Medical—ER-SPEC Product Presentation published Apr. 16, 2014 (12 pages).

OBP Medical—ER-SPEC Brochure published Apr. 11, 2013 (2 pages).

OBP Medical—ER-SPEC Brochure published Feb. 4, 2013 (2 pages).

OBP Medical—ER-SPEC Brochure, Light Source Now 10X Brighter published Jan. 23, 2013 (1 page).

Redefining illumination, Eikon LT Adapt SE For optimal precision and protection (2019), Stryker, www.stryker.com/surgical (3 pages).

(56) References Cited

OTHER PUBLICATIONS

Supplementary European Search Report dated Oct. 6, 2021 issued in European Application No. 19757432.0, 15 pages.
Opposition, "Brief Communication," in European Appln. No. 16804432.9, mailed on Aug. 1, 2025, 26 pages.
Opposition, "CLEAR-TRAC: Single-Use Surgical Retractor with Built-In Light Source," Exhibit D6 in European Appln. No. 16804432.9, Apr. 16, 2014, mailed on May 30, 2024, 2 pages.
Opposition, "Notice of Opposition against European Patent No. 3302292," in European Appln. No. 16804432.9, mailed on May 30, 2024, 26 pages.
Opposition, "OBP Medical CLEAR-TRAC," Exhibit D7 in European Appln. No. 16804432.9, available on or before Jun. 26, 2014, via Internet Archive: Wayback Machine URL<https://web.archive.org/web/20140626121552mp_/https://obpmedical.com/product/clear-trac/#hospital>, mailed on May 30, 2024, 3 pages.
Opposition, "Reply to Observations made by the Patent Proprietor(s)," in European Appln. No. 16804432.9, mailed on Feb. 26, 2025, 13 pages.

* cited by examiner

ILLUMINATED DUAL-BLADE RETRACTOR

CROSS-REFERENCE TO RELATED APPLICATIONS

This application is a continuation of U.S. patent application Ser. No. 17/192,935, filed on Mar. 5, 2021, which is a continuation of U.S. patent application Ser. No. 16/800,227 filed on Feb. 25, 2020. The entire contents of these applications are incorporated herein by reference.

FIELD OF INVENTION

The present invention relates to a dual-blade retractor, and more particularly, to a portable illuminated dual-blade retractor with illumination at both blades and to a dual-blade retractor with smoke evacuation provided at both blades.

INTRODUCTION

A dual-blade retractor, also referred to as an Army-Navy retractor, is a surgical instrument that includes a handle with a blade extending from each end of the handle. Typically, dual-blade retractors include a shorter blade extending from one end of the handle and a longer blade extending from another end of the handle. Dual-blade retractors can be utilized in different types of surgeries and provide flexibility by having two blades of different sizes.

Surgical and medical procedures usually require illumination of a desired surgical field in order to improve visibility for the surgeon. Traditionally, illumination was provided using overhead lighting or head mounted fiber optic systems. In addition, medical devices, such as retractors, that include illumination systems have been used in the field. For example, US Patent Application Publication Nos. 2016-0354072 and U.S. Pat. No. 10,512,519, owned by the same applicant herein and incorporated herein by reference, disclose single-blade retractors that include an illumination assembly for illuminating a surgical field during use.

In addition, surgical procedures often require use of electrocautery devices and other devices, which produce smoke that interferes with visibility of the surgical field. The single-blade retractors of the above-mentioned ’072 publication and the ’519 patent include a smoke evacuation assembly for suctioning off smoke generated during surgical procedures.

SUMMARY OF THE INVENTION

The present invention provides a dual-blade retractor with an illumination assembly that includes at least one direct light source on each blade of the retractor and an ergonomic and space-efficient switching assembly that allows for individual controls of the light source(s) on each blade. In addition, the present invention provides a dual-blade retractor that has a smoke evacuation assembly for providing dedicated smoke evacuation for each blade of the retractor. Moreover, the smoke evacuation assembly is configured such that it does not interfere with the field of view of either side of the retractor.

Specifically, in accordance with the present invention, the dual-blade retractor comprises a handle having a first end and a second end, a first blade extending from the first end of the handle, a second blade extending from the second end of the handle, and an illumination assembly including one or more first light sources provided on the first blade and one or more second light sources provided on the second blade, wherein the dual-blade retractor is configured to house therein an internal power source for supplying energy to the one or more first and second light sources. In some embodiments, the handle is configured to house the internal power source.

In certain embodiments, the illumination assembly has a plurality of the first light sources oriented to emit light at different angles relative to the first blade, and a plurality of the second light sources oriented to emit light at different angles relative to the second blade. In certain configurations of the dual-blade retractor, the first blade includes a first cover having one or more openings corresponding in position to the one or more first light sources, and the second blade includes a second cover having one or more openings corresponding in positions to the one or more second light sources.

In certain embodiments, the illumination assembly is configured to selectively control the one or more first light sources when the first blade is in use and the one or more second light sources when the second blade is in use. The illumination assembly may also include a control circuit configured to electrically connect with the one or more first light sources and the one or more second light sources, and the dual-blade retractor is configured so as to position the internal power source to overlap with the control circuit. In some embodiments, the dual-blade retractor has a removable cover configured to eject the internal power source from the dual-blade retractor when the removable cover is removed.

In certain embodiments, the one or more first light sources are mounted on a first flexible circuit configured to dissipate heat generated by the one or more first light sources, and similarly, the one or more second light sources are mounted on a second flexible circuit configured to dissipate heat generated by the one or more second light sources. In some embodiments, the dual-blade retractor also includes a smoke evacuation assembly configured to selectively provide suction to the first blade and the second blade.

The present invention is also directed to a dual-blade retractor comprising a handle having a first end and a second end, a first blade extending from the first end of the handle, a second blade extending from the second end of the handle, and a first smoke evacuation conduit configured to provide suction at the first blade, and a second smoke evacuation conduit, separate from the first smoke evacuation conduit, configured to provide suction at the second blade. In some embodiments, the first smoke evacuation conduit extends between a first inlet provided on the first blade and a first outlet provided on one of the handle and the second blade. Similarly, the second smoke evacuation conduit extends between a second inlet provided on the second blade and a second outlet provided on one of the handle and the first blade. The first outlet may be provided at a joint between the handle and the second blade, and the second outlet may be provided at a joint between the handle and the first blade. The dual-blade retractor also includes an adapter configured to fluidly couple one or more of the first outlet and the second outlet to a vacuum source.

In some embodiments, the dual-blade retractor includes a first blade cover configured to attach to the first blade and a second blade cover configured to attach to the second blade. In these embodiments, the first inlet and the second outlet are provided in the first blade cover, and the second inlet and the first outlet are provided in the second blade cover. In certain embodiments, the first smoke evacuation conduit includes at least one first tube and the second smoke evacuation conduit includes at least one second tube. The first and second tubes may extend substantially parallel to one another within the handle.

The present invention is also directed to a dual-blade retractor comprising a handle having a first end and a second end, a first blade extending from the first end of the handle, a second blade extending from the second end of the handle, a smoke evacuation assembly configured to selectively provide suction to the first blade and the second blade, wherein the smoke evacuation assembly includes at least one port configured to connect to a vacuum source, and wherein when the smoke evacuation assembly provides suction to one of the first and second blades, the at least one port does not obstruct a field of view around the one of the first and second blades. In some embodiments, the at least one port includes an opening in an outer housing of the dual-blade retractor and the smoke evacuation assembly also includes a removable adapter insertable into the opening and configured to connect to the vacuum source.

In certain embodiments, the at least one port includes a first port for providing suction to the first blade and a second port for providing suction to the second blade. The first port comprises a first opening provided on one of the handle and the second blade and the second port comprises a second opening provided on one of the handle and the first blade. The smoke evacuation assembly further includes a removable adapter configured to be inserted into at least one of the first opening and the second opening and to connect to the vacuum source. In some embodiments, the smoke evacuation assembly further includes first tubing extending between the first port and a first smoke evacuation inlet on the first blade and second tubing extending between the second port and a second smoke evacuation inlet on the second blade. The first opening may be provided at a joint between the handle and the second blade and the second opening may be provided at a joint between the handle and the first blade. In some embodiments, the first port further comprises a first socket provided at the first opening and configured to engage with the removable adapter and the second port further comprises a second socket provided at the second opening and configured to engage with the removable adapter.

In some embodiments, the first blade and the second blade extend from the handle in a first direction. In addition, the dual-blade retractor may also include an illumination assembly including one or more first light sources provided on the first blade and one or more light sources provided on the second blade.

The present invention is further directed to a dual-blade retractor comprising a handle having a first end and a second end, a first blade extending from the first end of the handle, a second blade extending from the second end of the handle, and an illumination assembly including one or more first light sources provided on the first blade, one or more second light sources provided on the second blade, and a switch for controlling the illumination assembly, wherein the one or more first light sources and the one or more second light sources are selectively controlled using the same switch. The switch may be a rocker switch and/or a sliding switch. The switch is configured to control one or more of ON/OFF state and brightness of the one or more first light sources and the one or more second light sources.

In some embodiments, the first and second blade extend from the handle in a first direction, and wherein the switch is provided in a first surface of the handle facing in the first direction. In certain embodiments, the dual-blade retractor further includes an activator different from the switch, with the activator being configured to move between a first position and a second position. In the first position the illumination assembly is deactivated and the switch is inoperable to control the illumination assembly, and in the second position, the illumination assembly is activated and the switch is operable to control the illumination assembly.

BRIEF DESCRIPTION OF THE DRAWINGS

The above and other features and aspects of the present invention will become more apparent upon reading the following detailed description in conjunction with the accompanying drawings, in which.

DETAILED DESCRIPTION

Figure 1:
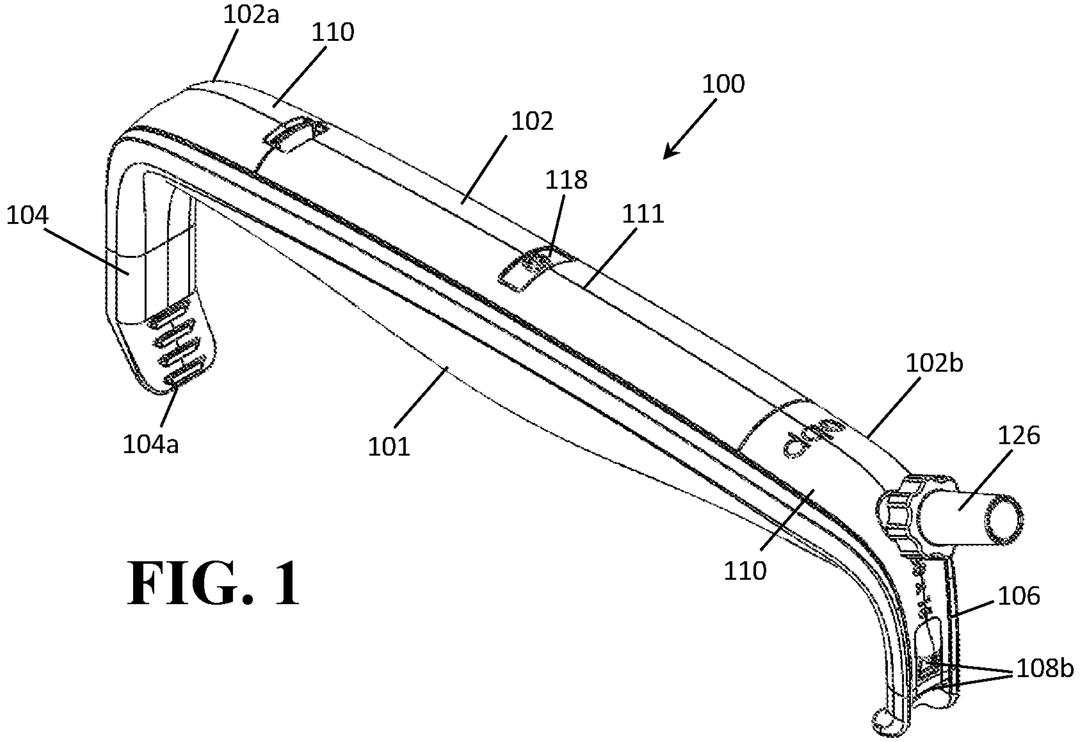
FIGS. 1 and 2 show the dual-blade retractor of the present invention, viewed from each end.

Drawings have been used herein to depict select exemplary embodiments. For the sake of clear illustration, many practical details are explained together in the description below. However, it should be appreciated that those details should not be used to limit the scope of any claims that issue in connection with this application. In some embodiments, certain details are not essential.

Moreover, for the sake of drawing simplification, some customary structures and elements in the drawings have been shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art. It should be further understood that terms, such as those defined in commonly used dictionaries, should be interpreted as having a meaning that is consistent with their meaning in the context of the relevant art and the present description, and should not be interpreted in an idealized or overly formal sense unless expressly so defined herein.

Figure 2:
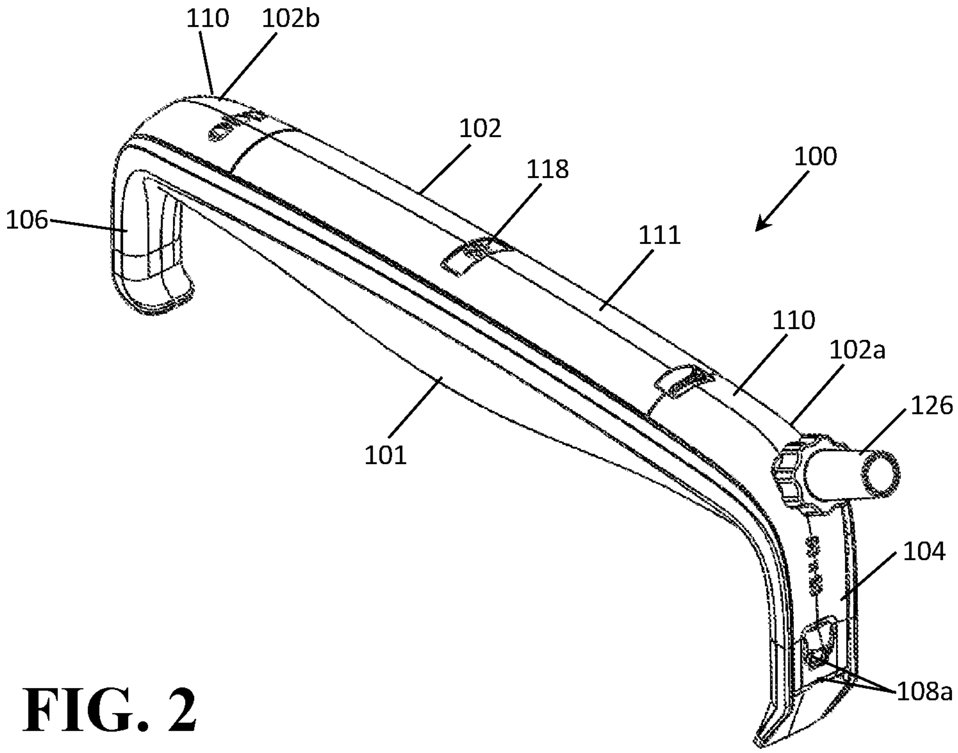
Figure 3:
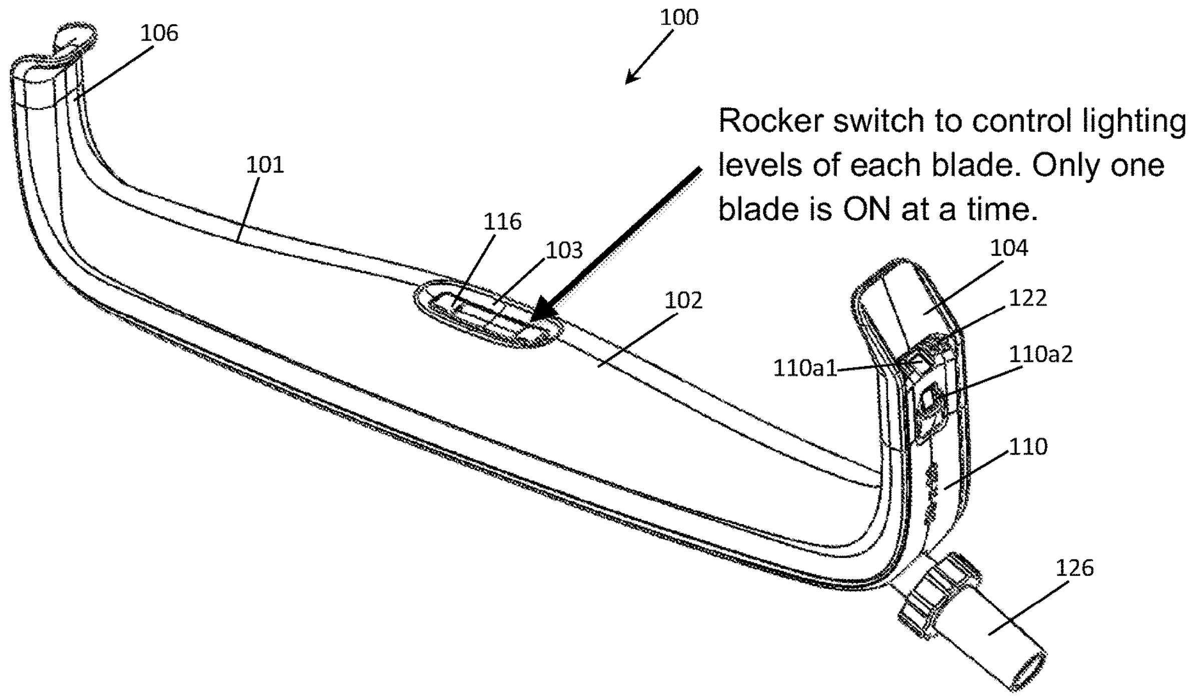
FIG. 3 shows the dual-blade retractor of FIGS. 1 and 2 viewed from an opposite side.
Figure 5A:
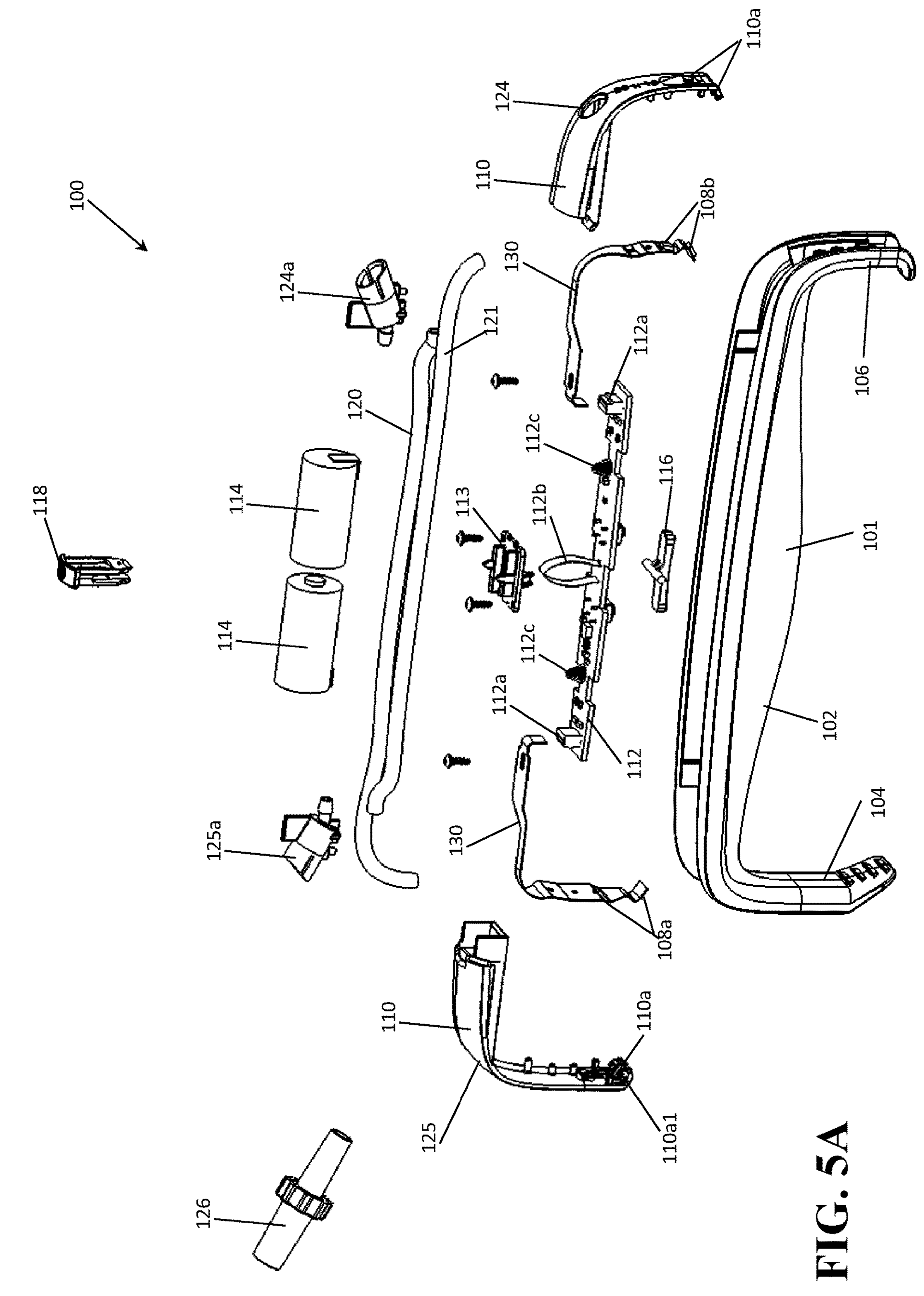
FIGS. 5A-5B show exploded views of components of the dual-blade retractor of FIGS. 1-3.
Figure 5B:
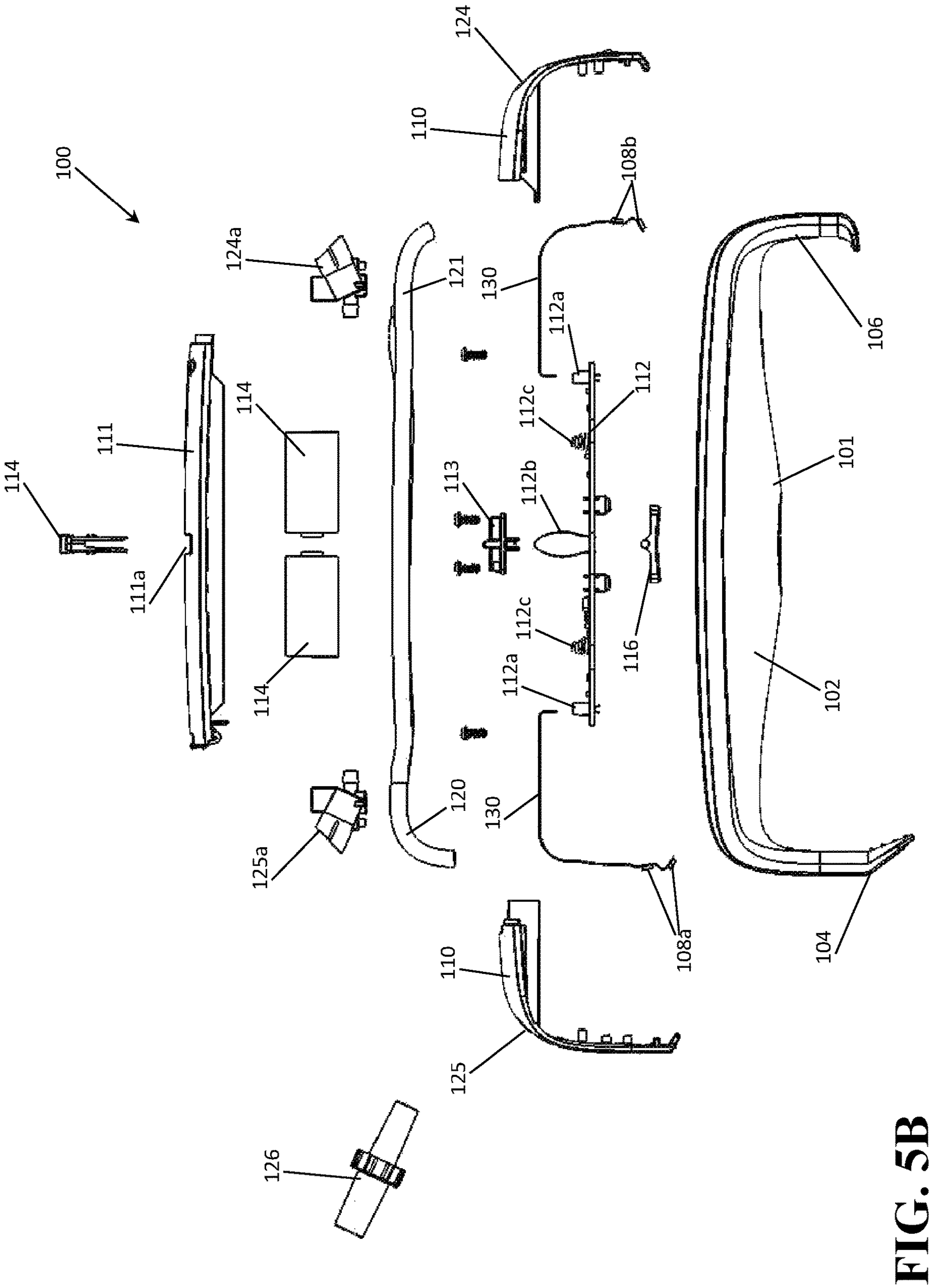

The present invention is directed to a dual-blade retractor. FIGS. 1-3 show different views of the dual-blade retractor 100 in accordance with the present invention and FIGS. 5A-5B show exploded views of the retractor 100 of FIGS. 1-3. As shown, the retractor 100 includes a handle 102 having a first end **102*a* and a second end 102*b*, a first blade 104 extending from the first end 102*a* of the handle 102 and a second blade 106 extending from the second end 102*b* of the handle 102. In the present illustrative embodiment, the first and second blades 104, 106 extend from the respective ends of the handle 102 in the same general direction. However, in other embodiments, the blades may extend in different directions, e.g., opposing directions, or may be configured to rotate relative to the handle 102. In addition, in this illustrative embodiment, the first and second blades 104, 106 are different in size, with the first blade 104 being longer and wider than the second blade 106. For example, the first blade 104 may have a length of about 50 mm and a width of about 20 mm, while the second blade 106** may have a length of about 30 mm and a width of about 15 mm.

In other embodiments, the first and second blades 104, 106 may have the same width and length, or may have the same length but different widths, or the same width but different lengths. In any case, the widths and lengths of the two blades 104, 106 may be varied depending on the application and intended use of the retractor. Moreover, although in this embodiment, the first and second blades 104, 106 are integrally formed with the handle, permanently attached to the handle 102 in this embodiment, in other embodiments, the first blade 104 and/or second blade 106 may be detachable from the handle 102 and may be interchangeable with other blades, e.g., blades of different widths and/or lengths.

As shown in FIGS. 1-2, the first blade 104, which is the longer and wider blade, includes a non-slip pattern including a plurality of non-slip projections or ridges 104*a* on its surface to provide better grip against tissue being retracted. In this illustrative embodiment, the second blade 106 does not include any non-slip projections or ridges, as shown in FIG. 1. However, it is contemplated that in other embodiments, the non-slip pattern may be included on one or more surfaces of the second blade 106. In addition, in the illustrative embodiment shown in FIGS. 1-2, the non-slip pattern 104*a* is provided on one surface of a distal tip of the first blade 104, while other surfaces do not include such non-slip pattern. In other embodiments, the location of the non-slip pattern may vary and the non-slip pattern may be provided on the entire surface or on a substantial area of the surface of the first blade 104, or may be provided on both surfaces of the first blade 104, either on the distal tip or on the whole surface of the blade. In some embodiments, the first blade 104 may include a first type of non-slip pattern on its tip portion and a different, second type of non-slip pattern on other portions thereof, or the first blade 104 may include one type of non-slip pattern on one surface and another type of non-slip pattern on the opposing surface. The type of non-slip pattern shown in FIG. 1 provided on the distal tip of the first blade 104 comprises a plurality of elongated ridges each of which has an inclined surface inclined away from the distal end of the first blade 104. This non-slip pattern is described in U.S. Pat. No. 10,512,519, which is assigned to the applicant herein and which is incorporated herein by reference. This and other types of non-slip patterns described in the '519 patent may be used on the surface(s) of the first and second blades 104, 106 of the dual-blade retractor 100.

As can be seen in FIGS. 1, 2 and 5A-5B, the handle 102 and the two blades 104, 106 form an outer housing that encloses or partially encloses components of an illumination assembly and of a smoke evacuation assembly described in more detail below. The outer housing includes a main body 101, which forms the handle and the blades 104, 106, blade covers 110, each of which covers a portion of a top surface of the respective blade 104, 106 and a top surface of a joint between the handle and the respective blade 104, 106, and a battery cover 111 which covers the remaining portion of the top surface of the handle 102. The main body 101, the blade covers 110 and the battery cover 111 are formed from plastic or polymer materials and may include glass or carbon fibers. For example, the main body 101, blade covers 110 and/or the battery cover 111 may be formed from ABS (acrylonitrile butadiene styrene) or polyarylamide polymer and may be glass-fiber reinforced, e.g., 50% by weight or more of glass fiber. Other polymer or plastic materials, which are preferably non-conductive and radiolucent, may be used for the main body 101, blade covers 110 and/or battery cover 111, and some exemplary materials are described in U.S. Pat. No. 10,420,538, assigned to the same assignee herein and incorporated herein by reference.

As mentioned above, the dual-blade retractor 100 of FIGS. 1-5B includes an illumination assembly that provides illumination from each blade 104, 106 and in which illumination in each blade is individually controlled. In addition, the illumination assembly of the present invention includes an internal, on-board power source 114 for powering the illumination assembly, making the dual-blade retractor cordless and portable, so that the dual-blade retractor is not dependent on an external power supply. In this way, the dual-blade retractor 100 can be used anywhere and the operator is not limited to locations or orientations in which the retractor can be connected to an external power supply.

The illumination assembly includes at least one direct light source, such as an LED, provided on the first blade 104 and/or at least one direct light source provided on the second blade 106. The illumination assembly further includes the power source 114, such as batteries, housed within the handle 102 of the dual-blade retractor 100 or in other portions of the outer housing, and one or more operating members 116, e.g. a switch, for controlling the ON/OFF state, brightness and/or color of the direct light sources.

In the present illustrative embodiment of FIGS. 1-3, the illumination assembly includes two direct light sources 108*a* provided on the first blade 104 and two direct light sources 108*b* provided on the second blade 106, with a first direct light source on each blade 104, 106 being oriented at a different angle from a second direct light source on the same blade 104, 106. In this example, the first direct light source is positioned near the distal end of the blade 104, 106 and is oriented so as to emit light along or substantially parallel to the blade toward the distal end of the blade, while the second light source is positioned further away from the distal end of the blade 104, 106 and is oriented so as to emit light at an angle to the blade to provide some illumination above the blade without creating a black light or glare to the user.

As discussed above, each blade 104, 106 includes the blade cover 110 that encloses a portion of the smoke evacuation assembly and a portion of the illumination assembly adjacent to the blade 104, 106. The blade cover 110 includes a plurality of openings 110*a* corresponding in positions to the direct light sources 108*a*, 108*b* of the illumination assembly so that the direct light sources are positioned within the corresponding openings 110*a*. As can be seen in FIGS. 3 and 5A-B, the blade cover 110 includes an angled tip, or lip portion, at its distal end which includes an opening 110*a*1 corresponding to the first direct light source. The opening 110*a*2 for the second direct light source is provided in main portion, i.e., top surface, of the blade cover 110 and may include a partial hood or shield adjacent its proximal edge to shield light from being emitted in the direction of the user.

As shown in FIGS. 5A-5B, the light sources 108*a* are mounted on a flexible circuit 130 which holds the light sources 108*a* in their respective positions and orientations within the corresponding openings 110*a* in the blade cover 110, and which electrically connects the light sources 108*a* to a PCB controller 112 provided within the handle 102. The light sources 108*b* are similarly mounted on the flexible circuit 130. In some embodiments, LED flex circuits with improved heat dissipation, as described in U.S. Pat. No. 10,512,519 and incorporated herein by reference, are used as the flexible circuits 130 with the light sources 108*a*, 108*b* mounted thereon on the respective blades 104, 106. Specifically, heat generated by the light sources is absorbed and dissipated by the flexible circuits 130. The blades 104, 106 and/or the blade covers 110 may include projections or ribs formed on their internally facing surfaces for positioning and holding the flexible circuits 130 within the outer housing.

As shown in FIGS. 5A and 5B, the illumination assembly also includes the PCB controller 112 that controls the illumination assembly, the power source 114 for supplying energy to the direct light sources 108*a*, 108*b*, and the operating member 116. The construction of the PCB controller 112 is similar to that of a PCB assembly described in the U.S. Pat. No. 10,512,519, which is incorporated herein by reference. In the present invention, the PCB controller 112 has two sets of flex circuit connectors 112*a*, which are used for connecting the flexible circuits 130 with the direct light sources 108*a*, 108*b* thereon to the PCB controller 112. The PCB controller 112 also includes a central contact 112*b* and springs or other electrical contacts 112*c* for electrically connecting the batteries 114 to the PCB controller 112. In some embodiments, the PCB controller 112 is positioned and held within the handle 102 by internal projections or ribs 102*c* (visible in FIGS. 4B and 4C) formed on the internal surfaces of the handle 102. In some embodiments, in addition to or instead of the internal projections, a PCB mounting bracket 113 is used for positioning and/or attaching the PCB controller in the handle 102 using screws or other suitable fasteners.

As shown in FIG. 3, the operating member 116 in the present embodiment comprises a rocker switch which can be operated to control the ON/OFF state and lighting levels of the direct light sources on each blade. The operating member 116 selectively controls the light sources on the first blade 104 when the first blade is being used and selectively controls the light sources on the second blade 106 when the second blade is being used. Specifically, the operating member 116 is configured so that the light sources on only one of the blades are turned ON while the light sources on the other blade are OFF. In one embodiment, the rocker switch 116 includes two buttons or two sides of a rocker, each of which is used for controlling the ON/OFF state and the brightness level of the light sources on one blade. In such embodiments, the user can press one of the buttons or one side of the rocker to turn ON the light source(s) on the corresponding blade and then press the button/side again in order to control the ON/OFF state of the individual light sources and/or the brightness of the light sources on the corresponding blade, while the light sources on the other blade are turned OFF. Repeated pressing of the button or the side of the rocker controls the turning ON and OFF of the individual light sources, e.g., a sequence of the light sources being turned ON/OFF, and in some embodiments controls the level of brightness of the light sources, e.g., increases brightness by repeatedly pressing the button or side of the rocker.

In another embodiment, the switch 116 includes a slide switch so that sliding the switch to one side turns ON the light sources, either at the same time or individually one by one, and increases the level of brightness of the light sources on one blade, and sliding the switch to the other side turns ON the light sources on the other blade, either at the same time or individually one by one, and increases the level of brightness of these light sources. The slide switch may be combined with a button or a similar operating member that can be pressed in order to select which of the light sources on the blade are turned ON. Other types of switches, such as potentiometers or a combination of a button and a potentiometer, may be used for controlling the light sources of the illumination assembly.

The above-described rocker and slide switches and the positioning of the switch on a bottom surface of the handle 102, as shown in FIG. 3, allow a user to operate the switch 116 with a thumb while holding the retractor in the same hand. This one-handed operation allows the user to control the lighting on the retractor while the retractor is being used to retract tissues. In addition, positioning the switch 116 within a recessed area 103 of the handle prevents the user from inadvertently operating the switch 116 while holding the retractor.

In the embodiment shown in FIGS. 1-5B, the dual-blade retractor 100 also includes a push-tab 118 of a push-tab assembly, which is used as a battery activator to activate the power source when in a "use" position and to de-activate the power source when in a "storage" position. Specifically, the push-tab assembly is used to control whether or not the illumination assembly can be turned ON by electrically disconnecting the power source(s) from circuitry of the illumination assembly in the "storage" configuration and by electrically connecting the power source(s) to the circuitry of the illumination assembly to close the circuit in a "use" configuration. The push-tab assembly also assists in removing the one or more power sources from the outer housing of the dual-blade retractor without requiring the user to come into physical contact with the power source by hooking around a portion of the power source(s), or otherwise physically engaging with the power source(s), when the power source(s) are housed in the outer housing and causing the power source(s) to be removed from the outer housing, or eject the power source(s), when the battery cover 111 is opened or removed from the main body 101.

When the retractor of FIGS. 5A-5B is assembled, the push-tab 118 is partially inserted into an opening 111*a* in the battery cover 111 so as to slip over and engage with the central contact 112*b* on the PCB controller 112. When the push-tab 118 is partially inserted into the opening 111*a*, the sides or legs of the push-tab 118 electrically separate the central contact 112*b* from the terminals of the batteries 114. In this way, the push-tab is in the "storage" position and electrically isolates the two batteries 114 from each other, i.e., breaks the circuit, so that the illumination assembly of the dual-blade retractor cannot be turned ON even if the switch 116 is in the ON position. However, when the push-tab 118 is fully inserted into the opening 111*a* in the battery cover 111 to be in the "use" position, the terminals of the batteries 114 electrically connect with the central electrical contact 112*b* through an opening in the push-tab 118 so that the illumination assembly can be turned ON using the switch 116. In addition, in the "use" position, the push-tab 118 engages with the terminals or other portions of the batteries 114 so that when the battery door 111 is opened or removed, the push-tab 118 forces the batteries 114 to be removed from the body 101 for disposal without requiring any physical contact between the user and the batteries 114. Additional details of the push-tab 118 and of the push-tab assembly and how it interacts with the electrical components of the illumination assembly and the power source(s) are described in U.S. Pat. No. 10,512,519, assigned to the same assignee herein and incorporated herein by reference. It is also contemplated that in some embodiments, the push-tab 118 does not need to be inserted fully into the opening 111*a* in the battery cover 111 to be in the "use" position, and that in other embodiments, the "use" and "storage" positions are reversed so that the push-tab 118 is pushed into the opening 111*a* for the "storage" position and pulled out of the opening 111*a* for the "use" position.

Figure 4A:
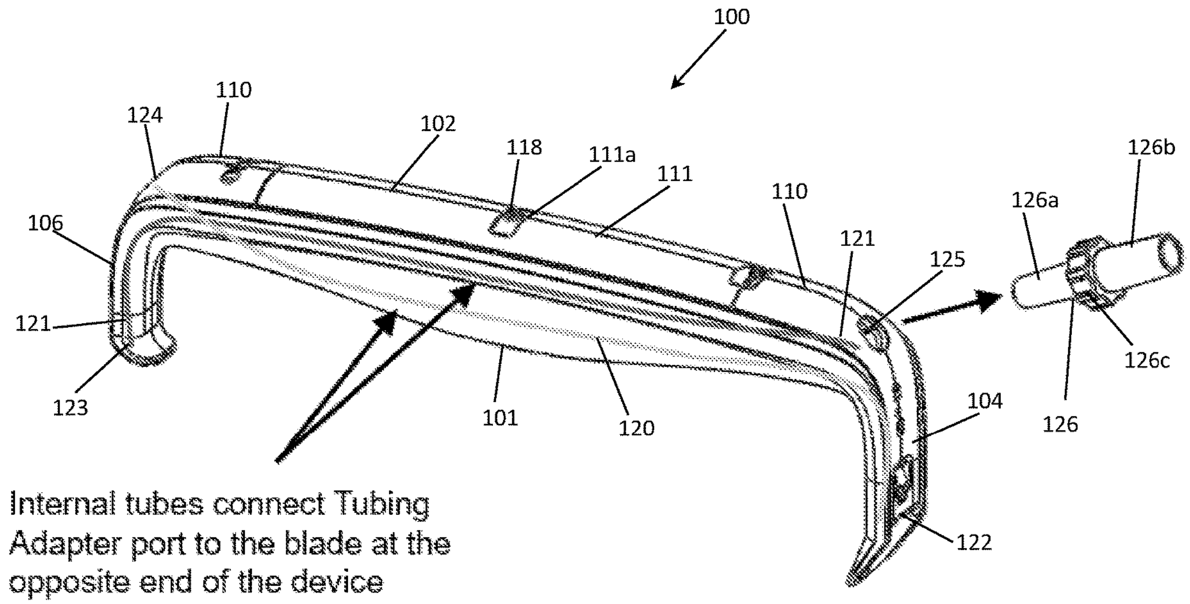
FIGS. 4A-4C demonstrate internal tubing of the smoke evacuation assembly and an adapter port of the dual-blade retractor of FIGS. 1-3.

As mentioned herein above, the dual-blade retractor also includes a smoke evacuation assembly that provides smoke evacuation/suction to each blade of the retractor 100 and which does not block the viewing field of the user when connected to a source of suction. As schematically shown in FIG. 4A and as further shown in FIGS. 4B-4C, internal tubing is provided within the outer housing of the dual-blade retractor to fluidly couple a smoke evacuation inlet near the distal end of each blade 104, 106 with a corresponding outlet opening near the opposing end of the handle 102. In one illustrative embodiment, first tubing 120 is provided within the outer housing of the retractor and extends between a first inlet 122 formed near the distal end of the first blade 104 and a first outlet opening 124 provided at or near the joint between the handle 102 and the second blade 106. As shown in FIGS. 1, 4A-C and 5A-B, the first outlet opening 124 is formed in the blade cover 110 for the second blade 106. Similarly, second tubing 121 is provided within the outer housing of the retractor and extends between a second inlet 123 formed near the distal end of the second blade 106 and a second outlet opening 125 at or near the joint between the handle 102 and the first blade 104. As shown in FIGS. 2, 4A-C and 5A-B, the second outlet opening 125 is formed in the blade cover 110 for the first blade 104. In some embodiments, the first and second outlets are provided in the handle 102, while in other embodiments, the first and second outlets are provided in the second and first blades, respectively.

Figure 4B:
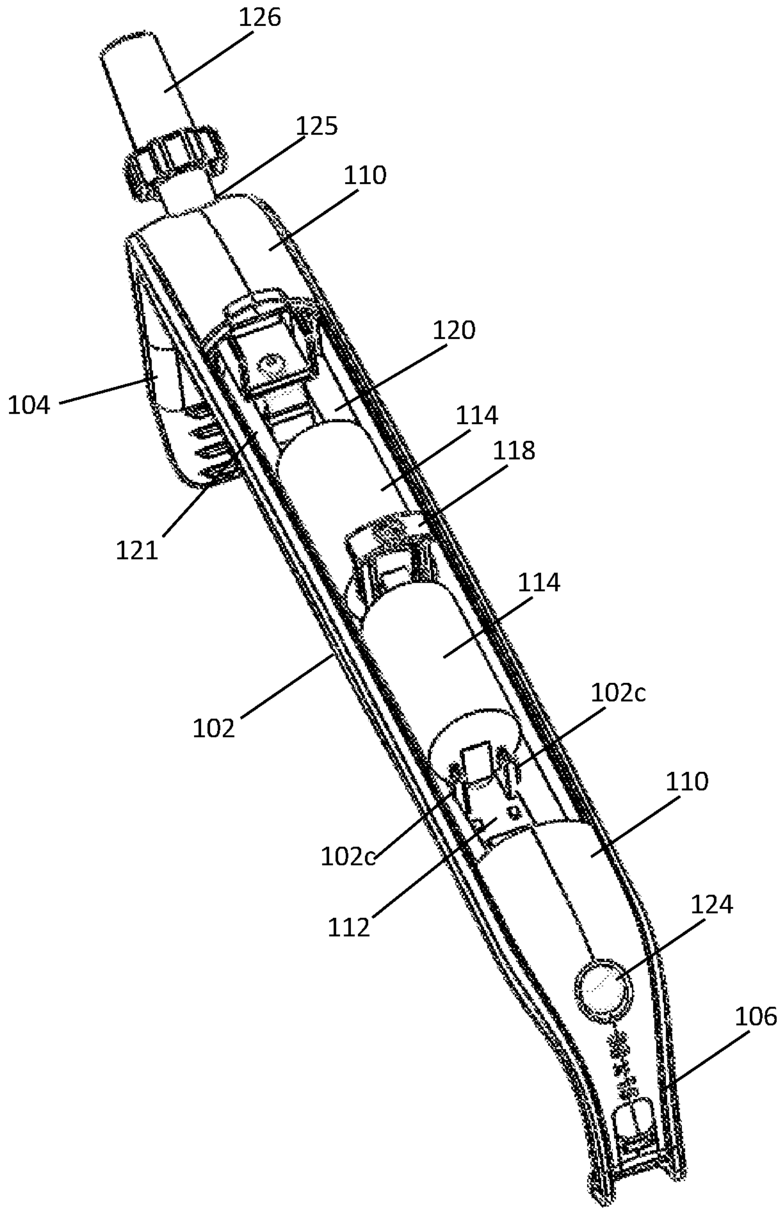
Figure 4C:
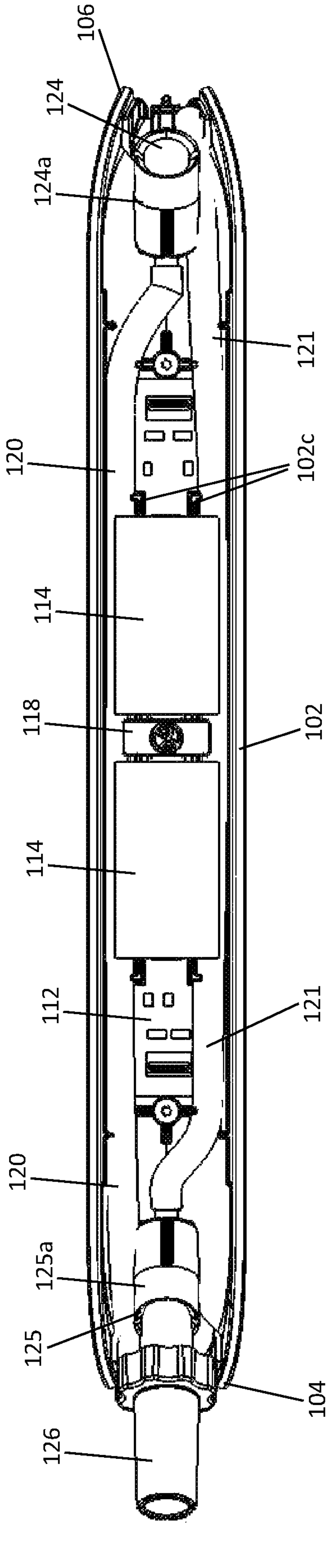

In some embodiments shown in FIGS. 4B-4C and 5A-5B, the first and second tubings 120, 121 each include a single tube so that the first and second tubings 120 and 121 run substantially parallel to one another within the handle 102 of the retractor. As can be seen in FIGS. 4B-4C, the first tubing 120 runs along one side of the handle while the second tubing 121 runs along the opposite side of the handle, with both first and second tubings 120, 121 being positioned on top of the PCB controller 112. The batteries 114 are centrally positioned and mounted on the PCB controller 112 so that the batteries 114 do not interfere with the first and second tubings 120, 121. In other embodiments, where space is available within the outer housing, the first and second tubings 120, 121 each includes a pair of tubes running in parallel from the respective blade through the handle 102 and combine at the respective outlet opening 124, 125. First and second tubings 120, 121 are flexible tubes that may be formed from plastics or silicone.

As can be seen in FIG. 3, the first inlet 122 is adjacent the distal end of the blade cover 110 for the first blade 104, and the lip or angled end of the blade cover 110 has a plurality of openings 110*b*, i.e., gratings, therein corresponding to the location of the first inlet 122. The gratings 110*b* prevent debris from entering the first tubing 120 and from blocking the flow path in the first tubing 120. Similarly, the second inlet 123 is adjacent the distal end of the blade cover 110 for the second blade 106, and the lip of the blade cover 110 includes similar gratings 110*b* therein corresponding to the location of the second inlet 123.

As shown in FIGS. 1-5B, each outlet opening 124, 125 does not protrude from the surface of the retractor in order to prevent the outlet port from interfering with the user's field of view. However, standard suction supply connections require a protruding barb in order to connect to the suction supply. In the present invention, a removable adapter port 126 is provided to enable connection between the respective outlet opening 124, 125 and the standard suction supply. The adapter port 126 comprises a substantially cylindrical body with a central bore, and includes a first end 126*a* sized and configured to be inserted into the outlet opening 124, 125 and a second end 126*b* sized and configured to couple to a standard suction supply. An annular ridge 126*c* having a gripping surface is provided between the first and second ends 126*a*, 126*b*.

In the embodiment shown in FIGS. 4A-4C, the first end 126*a* is sized so that it fits tightly within the outlet opening 124, 125 and is held therein by frictional forces. As shown in FIGS. 4C and 5A-5B, each outlet opening 124, 125 includes a sleeve member or socket 124*a*, 125*a* provided within the outlet opening 124, 125 and configured to connect with the corresponding tubing 120, 121. As can be seen in FIGS. 5A and 5B, each sleeve member or socket 124*a*, 125*a* includes side slits formed adjacent to its outlet edge to provide elasticity and flexibility so that the first end 126*a* of the adapter port 126 is held securely by the sleeve member or socket 124*a*, 125*a* when inserted into the outlet opening 124, 125.

In other embodiments, the first end 126*a* may have a thread thereon so that it can be screwed into the respective outlet opening 124, 125. In such embodiments, the sleeve members or sockets 124*a*, 125*a* would have corresponding threads on their inner surfaces to allow the first end 126*a* to be coupled therewith.

When inserted into the outlet opening 124, 125 and coupled with the sleeve member or socket 124*a*, 125*a* of the outlet opening, the first end 126*a* of the adapter is fluidly coupled with the respective tubing 120, 121 to provide suction to the blade in use. Since the adapter 126 is inserted into one of the outlet openings 124, 125 for use with the corresponding blade 104, 106 while the other outlet opening 124, 125 does not have a barb or adapter attached thereto, the adapter 126 and the rest of the smoke evacuation assembly does not obstruct the user's field of view along and around the retractor blade in use when the retractor is being used. In addition, since the adapter 126 can be removed and switched between the outlet openings 124, 125 when the blade 104, 106 being used is switched, the dual-blade retractor allows for smoke evacuation at each end thereof without having a fixed barb in the way of the field of view along and around the blade being used.

Figure 6A:
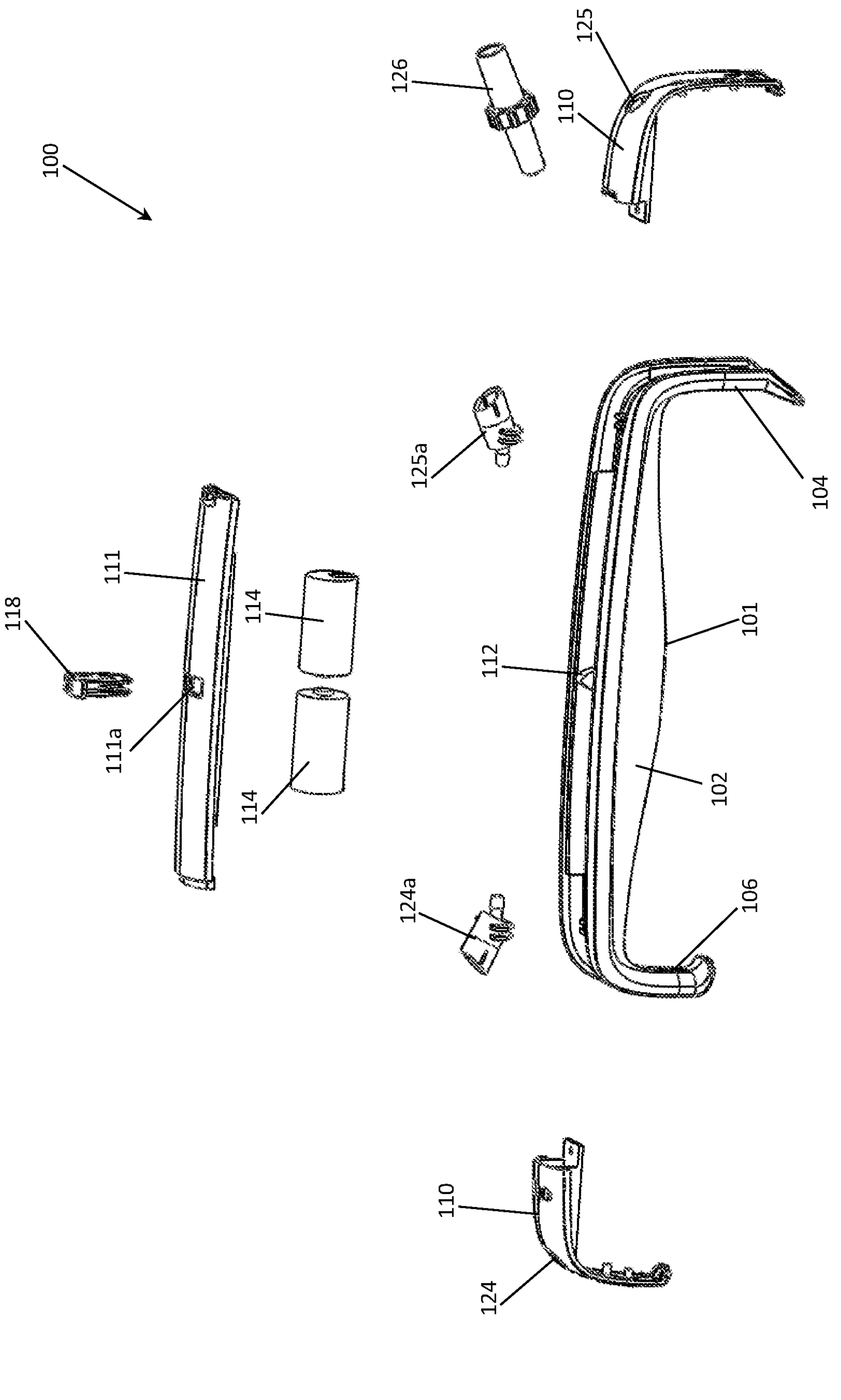
FIGS. 6A-6E show an exemplary assembly sequence of the components of the dual-blade retractor of FIGS. 1-3.

As mentioned above, FIGS. 5A-5B show exploded views of the dual-blade retractor 100 of the present invention. An exemplary assembly process for assembling the dual-blade retractor 100 of FIGS. 1-5B is shown in FIGS. 6A-6E. As shown in FIG. 6A, the rocker switch 116, the PCB controller 112 and the PCB bracket 113 are inserted into the handle 102 of the retractor main body 101, and the PCB bracket 113 is attached to the handle 102 using one or more fasteners, e.g., two screws. Prior to positioning the PCB controller 112 within the handle 102, the switch 116 may be electrically connected to the PCB controller 112, and then the PCB controller 112 with the switch 116 is positioned within the handle so that an outer portion of the switch 116 extends through a corresponding opening in the handle 112.

Figure 6B:
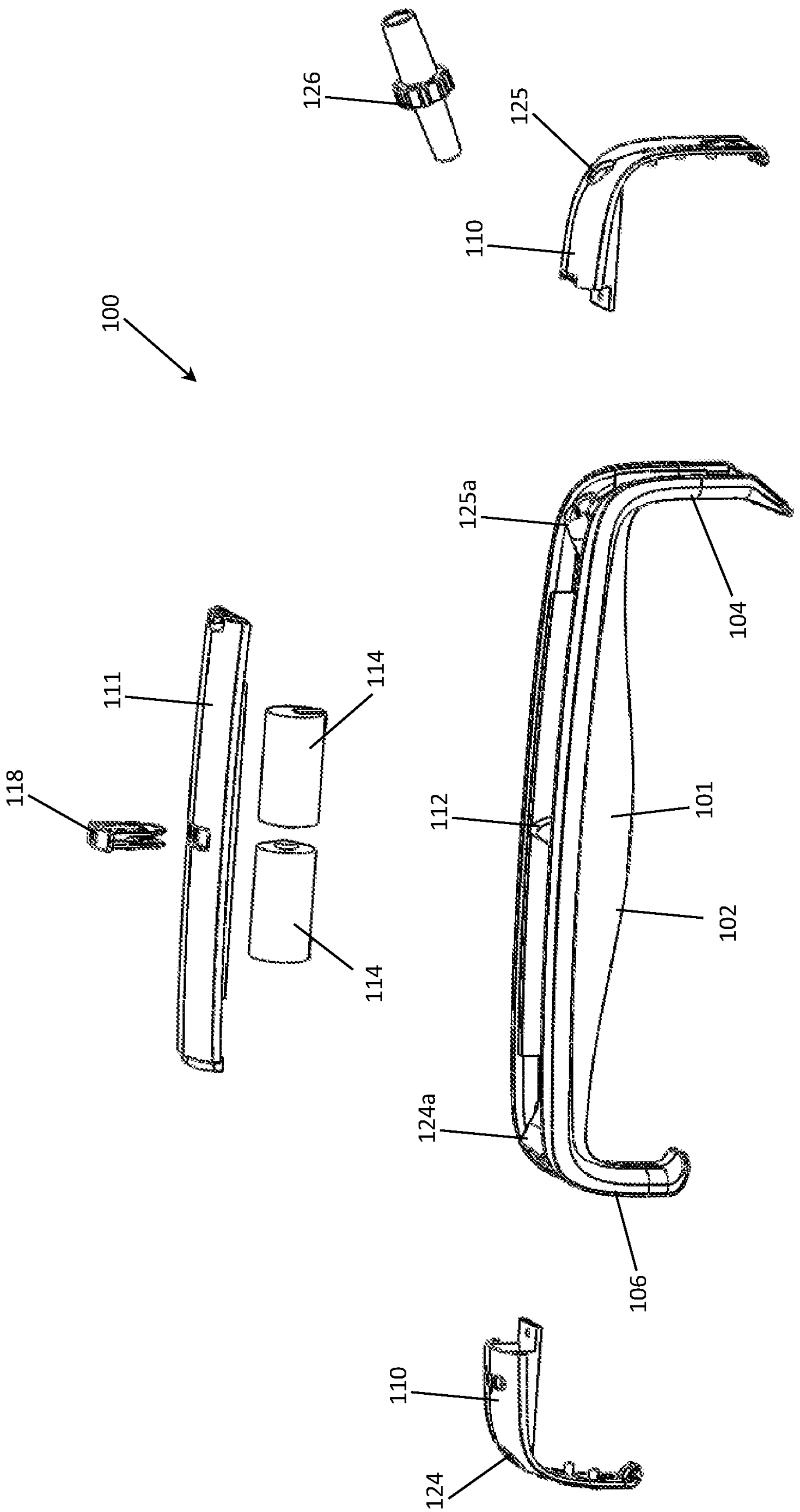

In the next step of the assembly process shown in FIG. 6B, sleeve members or sockets 124*a*, 125*a* and smoke evacuation tubing are installed into main body 101 of the retractor. Specifically, each smoke evacuation tube, which can be a plastic or a silicone tube, is attached to the respective sleeve member or socket 124*a*, 125*a*, and the sleeve members or sockets 124*a*, 125*a* are then installed within the main body 101 at or near the respective joint between the blade 104, 106 and the handle 102. The tubes are installed to run substantially parallel to one another within the handle and to the respective blades. In one embodiment, the tubes extend along opposite sides of the PCB controller within the handle, while in another embodiment, the tubes overlap or partially overlap with the PCB controller on each side thereof.

Figure 6C:
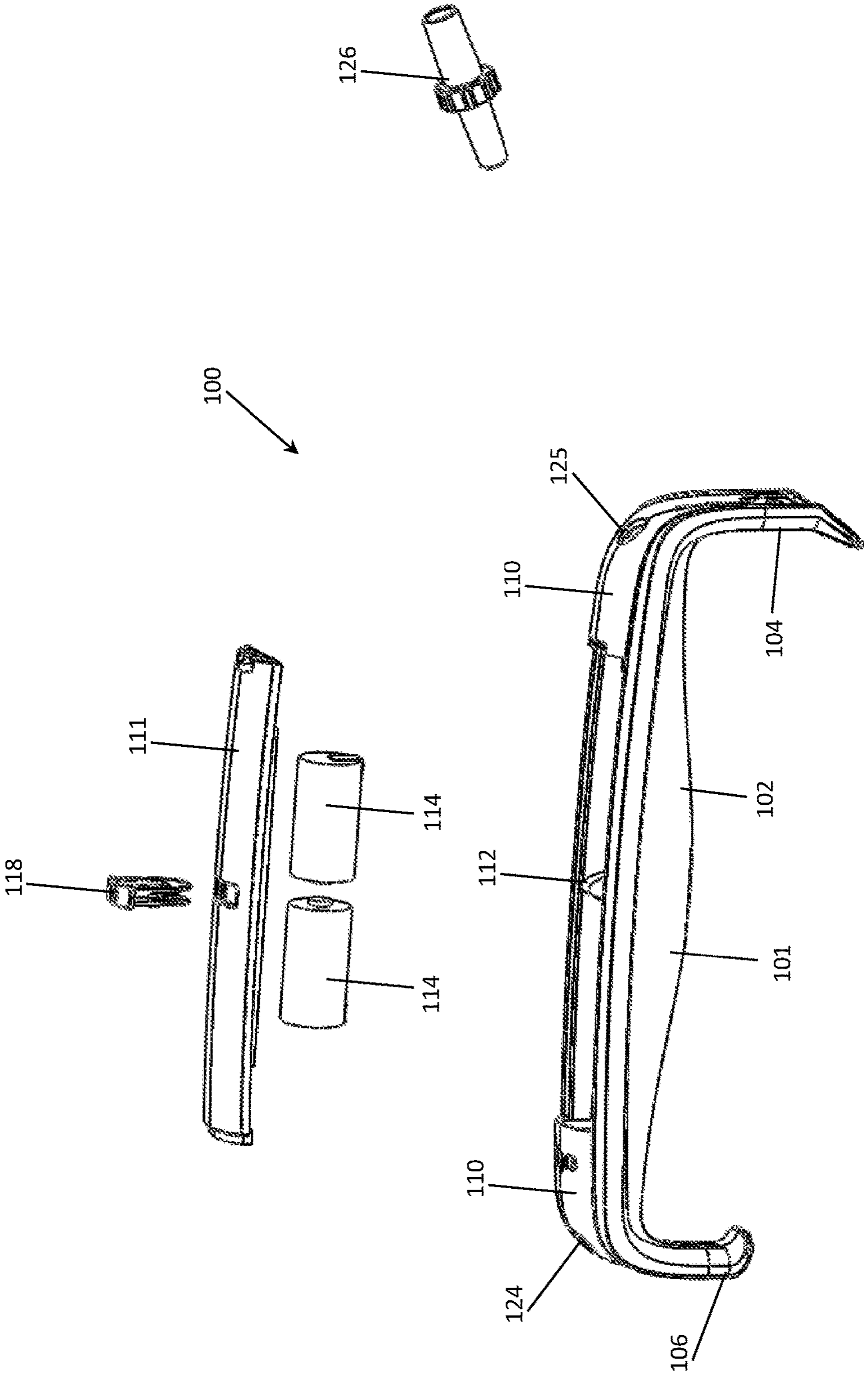

In the step of FIG. 6C, the flexible circuits with the light sources mounted thereon are installed on the blade covers 110 so that the light sources are exposed through corresponding openings in the blade covers 110. One or more fasteners, such as screws, may be used to attach the flexible circuits to the blade covers 110. In some embodiments, the flexible circuits are held to the blade covers by internal projections or ribs formed on the blade covers 110. The blade covers 110 are then attached to the main body 101 by snap fitting or interlocking with the main body 101, and/or by using one or more fasteners, such as screws, and/or by press fitting, as disclosed in the U.S. Pat. No. 10,512,519. The flexible circuits are electrically connected to the PCB controller by inserting exposed conductive traces on the flexible circuits into the flex circuit electrical connectors on the PCB controller.

Figure 6D:
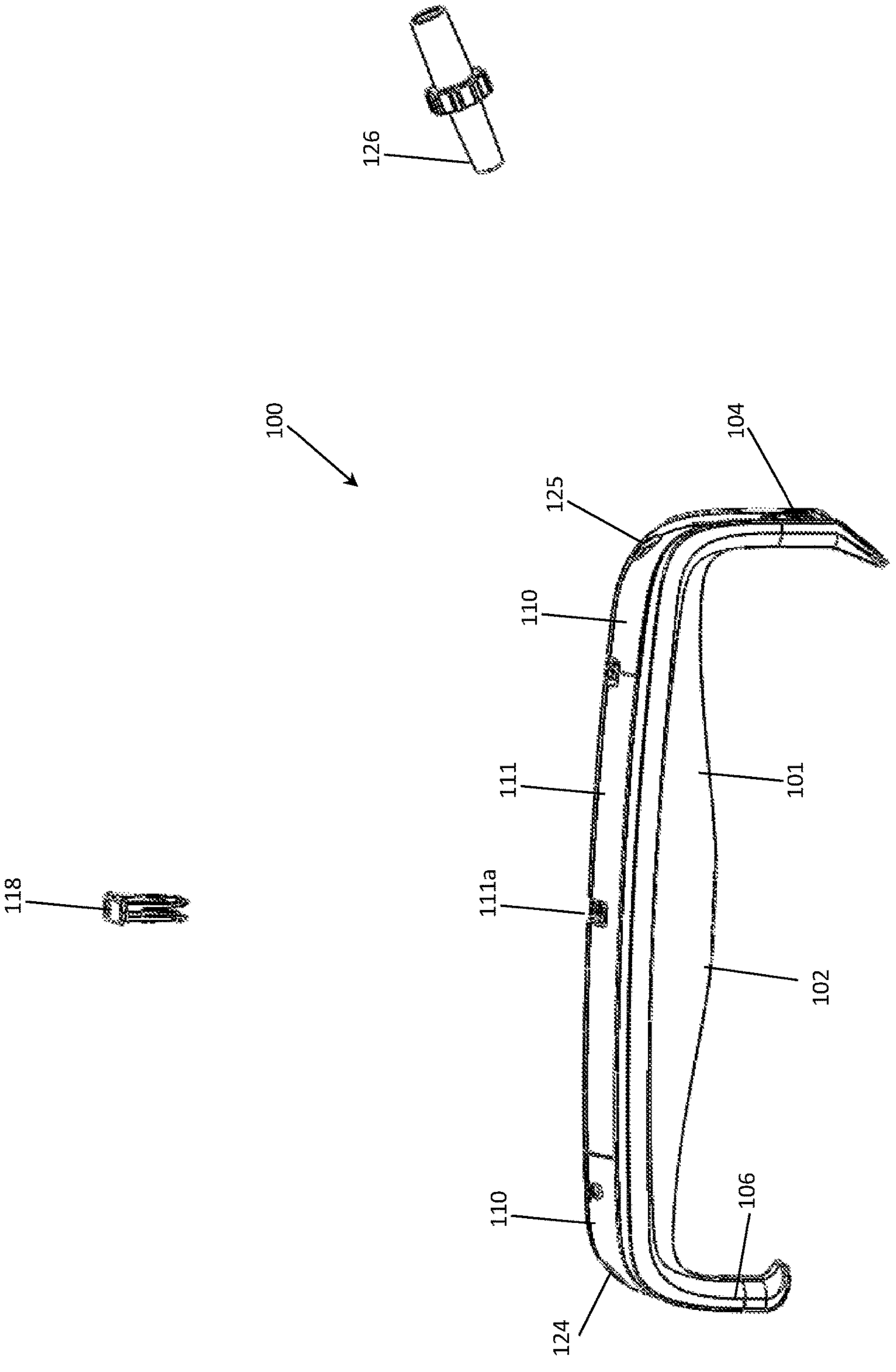
Figure 6E:
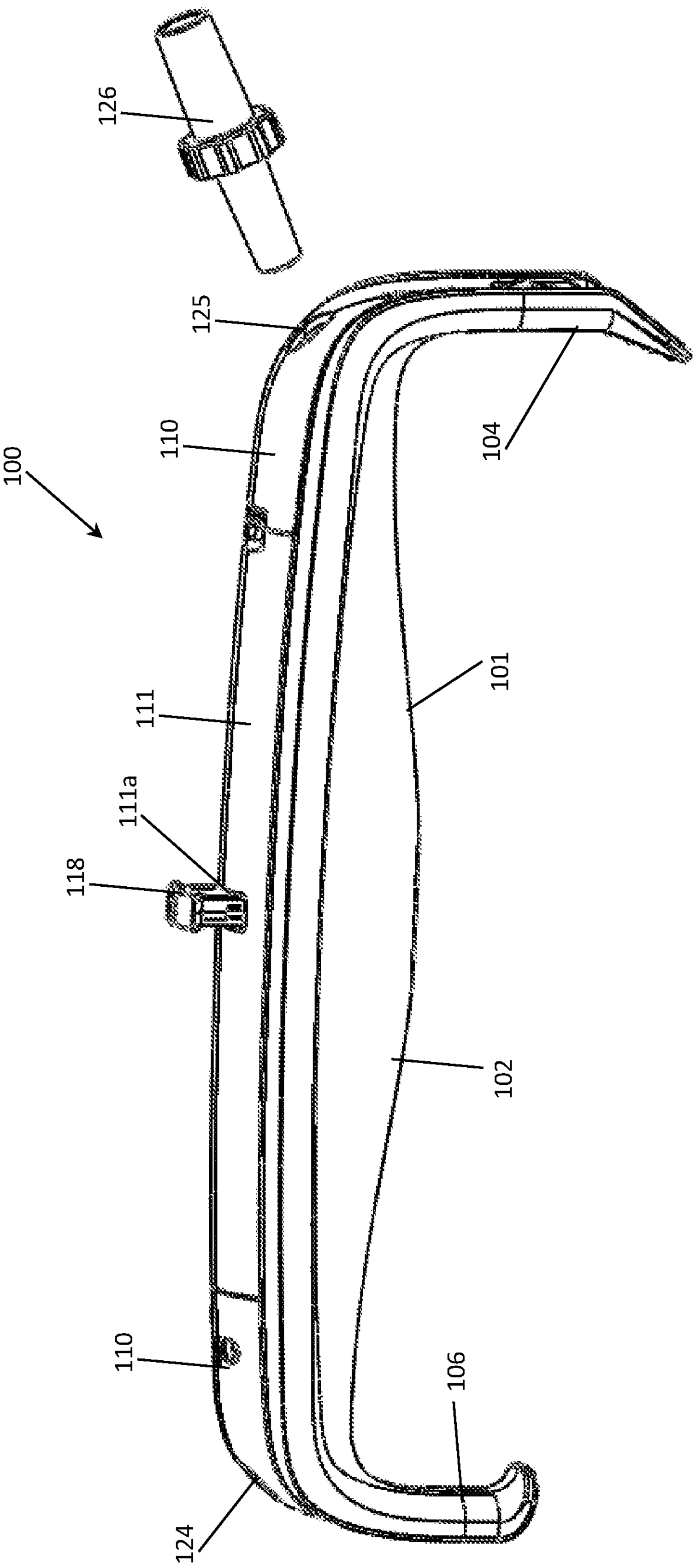

In the step of FIG. 6D, the batteries are installed into the handle 102 and the battery cover 111 is then attached to the main body 101. In some embodiments, the battery cover snaps into the main body 101 and can be detached by operating a catch or a similar fastening mechanism. Finally, in the step of FIG. 6E, the push-tab 118 is partially inserted into the opening 111*a* in the battery cover 111 for shipping. When the retractor is ready to be used, the push-tab 118 is fully pushed into the opening 111*a* so as to activate the batteries. Moreover, the removable adapter port 126 may or may not be pre-installed into one of the smoke evacuation openings 124, 125 for shipping.

The above-described assembly process may be varied so that some of the steps are performed before other steps. As discussed above, the assembled dual-blade retractor is a cordless, portable retractor that has on-board power and can be lighted on both blades. The dual-blade retractor also has a smoke evacuation assembly to provide dedicated smoke evacuation at each blade without having a fixed protruding port or barb that obscures the field of view of the user. Moreover, the dual-blade retractor is ergonomically constructed to allow for use of the retractor while being able to control the illumination assembly with one hand. In this regard, the lighting at both blades is controlled using the same operating member so as to simplify control of the illumination assembly. Although not shown in the figures, the dual-blade retractor may also include a flow control mechanism for controlling the suction in the retractor. The flow control mechanism may use the same operating member or switch as the illumination assembly or a separate switch.

Although certain embodiments have been described in considerable detail herein, other embodiments, variations, and modifications that fall within the spirit and scope of the invention will be apparent to those skilled in the art. Therefore, the scope of any claims allowed for this application should not be limited to any specific embodiments or to any non-claimed details of the embodiments described herein.

We claim:

1. A portable dual-blade retractor comprising:

a handle having a first longitudinal end at a first side of the handle and a second longitudinal end at a second side of the handle that is located opposite from the first side;

a first blade extending from the first end of the handle at the first side of the handle;

a second blade extending from the second end of the handle at the second side of the handle; and an illumination assembly comprising a control circuit, a first direct light source positioned on the first blade, and a second direct light source positioned on the second blade, wherein the control circuit is configured to electrically connect with the first direct light source and with the second direct light source, and the portable dual-blade retractor is configured to position the internal power source therein to overlap with the control circuit, and wherein the first and second direct light sources are individually controlled.

2. The portable dual-blade retractor according to claim 1, wherein the portable dual-blade retractor is cordless.

3. The portable dual-blade retractor according to claim 1, wherein the portable dual-blade retractor is configured to house therein an internal power source for supplying energy to the first and second direct light sources.

4. The portable dual-blade retractor in accordance with claim 1, wherein the first direct light source is oriented at a first angle with respect to the first blade to emit light at the first angle, wherein the second direct light source is oriented at a second angle with respect to the second blade to emit light at the second angle, wherein the illumination assembly further includes a third direct light source positioned on the first blade, wherein the third direct light source is oriented at a third angle with respect to the first blade to emit light at the third angle, wherein the illumination assembly further includes a fourth direct light source positioned on the second blade, wherein the fourth direct light source is oriented at a fourth angle with respect to the second blade to emit light at the fourth angle.

5. The portable dual-blade retractor in accordance with claim 4, wherein the first angle is different from the third angle, and wherein the second angle is different from the fourth angle.

6. The portable dual-blade retractor in accordance with claim 1, wherein:

the direct light source is mounted on a first flexible circuit configured to dissipate heat generated by the first direct light source, and the second direct light source is mounted on a second flexible circuit configured to dissipate heat generated by the second direct light source.

7. The portable dual-blade retractor in accordance with claim 1, further comprising a smoke evacuation assembly including a first smoke evacuation conduit configured to provide suction at the first blade, and a second smoke evacuation conduit configured to provide suction at the second blade.

8. The portable dual-blade retractor in accordance with claim 7, wherein the second smoke evacuation conduit is separate from the first smoke evacuation conduit, and the smoke evacuation assembly is configured to selectively provide suction to the first and second smoke evacuation conduits.

9. The portable dual-blade retractor in accordance with claim 7, wherein the smoke evacuation includes at least one port configured to connect to a vacuum source and wherein when the smoke evacuation assembly provides suction to one of the first and second blades, the at least one port does not obstruct a field of view around the one of the first and second blades.

10. The portable dual-blade retractor in accordance with claim 9, wherein the at least one port includes an opening in an outer housing of the retractor and said smoke evacuation assembly further comprises a removable adapter configured to be inserted into the opening and configured to connect to the vacuum source.

11. The portable dual-blade retractor in accordance with claim 1, wherein the first and second direct light sources are controlled using a switch.

12. The portable dual-blade retractor in accordance with claim 11, wherein the switch is provided in a recessed area of the handle.

13. The portable dual-blade retractor in accordance with claim 1, wherein a first position of the first blade is fixed with respect to the second blade, and wherein a second position of the second blade is fixed with respect to the first blade.

14. The portable dual-blade retractor in accordance with claim 13, wherein each of the first position and the second position is fixed with respect to the handle.

15. The portable dual-blade retractor in accordance with claim 1, wherein a first orientation of the first blade is fixed with respect to the second blade, and wherein a second orientation of the second blade is fixed with respect to the first blade.

16. The portable dual-blade retractor in accordance with claim 15, wherein each of the first orientation and the second orientation is fixed with respect to the handle.

17. The portable dual-blade retractor in accordance with claim 1, wherein at least a first portion of the first blade, at least a second portion of the second blade, and at least a third portion of the handle are integrally formed as one component.

18. A dual-blade retractor comprising:

an outer housing including:

a handle having a first longitudinal end at a first side of the handle and a second longitudinal end at a second side of the handle that is located opposite from the first side;

a first blade extending from the first end of the handle at the first side of the handle; and a second blade extending from the second end of the handle at the second side of the handle; and a smoke evacuation assembly configured to provide suction to the first blade and the second blade, wherein the outer housing includes at least one opening therein configured to accommodate a removable adapter therein so as to fluidly couple to a vacuum source and to provide suction to at least one of the first and second blades, and wherein the at least one opening does not protrude from a surface of the outer housing.

19. The dual-blade retractor in accordance with claim 18, wherein the smoke evacuation assembly further comprises the removable adapter configured to be inserted into the at least one opening.

20. The dual-blade retractor in accordance with claim 19, wherein the removable adapter comprises a body with a central bore and includes a first end sized to be inserted into the at least one opening and a second end configured to couple with the vacuum source.

21. The dual-blade retractor in accordance with claim 20, wherein the body of the removable adapter further includes an annular ridge on its outer surface between the first end and the second end.

22. The dual-blade retractor in accordance with claim 18, wherein the at least one opening is provided at a joint between the handle and one of the first and second blades.

23. The dual-blade retractor in accordance with claim 18, wherein the smoke evacuation assembly includes a first smoke evacuation conduit configured to provide suction to the first blade, and a second smoke evacuation conduit, separate from the first smoke evacuation conduit, configured to provide suction to the second blade.

24. The dual-blade retractor in accordance with claim 23, wherein a portion of the first smoke evacuation conduit and a portion of the second smoke evacuation conduit extend through the handle.

25. A dual-blade retractor comprising:

an outer housing including:

a handle having a first end and an opposing second end;

a first blade extending from the first end of the handle; and a second blade extending from the second end of the handle; and a smoke evacuation assembly configured to provide suction to the first blade and the second blade, wherein the outer housing includes an opening therein configured to accommodate a removable adapter therein so as to fluidly couple to a vacuum source and to provide suction to at least one of the first and second blades, and wherein the opening is provided at a joint between the handle and one of the first and second blades.

* * * * *